(12) United States Patent
Anderson et al.

(10) Patent No.: US 8,043,616 B2
(45) Date of Patent: Oct. 25, 2011

(54) SRAGE MIMETIBODY, COMPOSITIONS, METHODS AND USES

(75) Inventors: Glenn Mark Anderson, Norristown, PA (US); Robert Jordan, Thornton, PA (US); Kristen Picha, Malvern, PA (US)

(73) Assignee: Centocor, Inc., Malvern, PA (US)

(*) Notice: Subject to any disclaimer, the term of this patent is extended or adjusted under 35 U.S.C. 154(b) by 295 days.

(21) Appl. No.: 12/174,677

(22) Filed: Jul. 17, 2008

(65) Prior Publication Data

US 2009/0098122 A1 Apr. 16, 2009

Related U.S. Application Data

(62) Division of application No. 11/235,776, filed on Sep. 27, 2005.

(60) Provisional application No. 60/613,247, filed on Sep. 27, 2004.

(51) Int. Cl.
*A61K 39/395* (2006.01)

(52) U.S. Cl. .................................. 424/134.1

(58) Field of Classification Search ............... None
See application file for complete search history.

(56) References Cited

U.S. PATENT DOCUMENTS

| | | | |
|---|---|---|---|
| 5,202,424 A | 4/1993 | Vlassara et al. | |
| 5,428,130 A | 6/1995 | Capon et al. | |
| 5,656,272 A * | 8/1997 | Le et al. ................ | 424/133.1 |
| 5,852,174 A | 12/1998 | Vlassara et al. | |
| 5,864,018 A | 1/1999 | Morser et al. | |
| 6,004,958 A | 12/1999 | Brown et al. | |
| 6,465,422 B1 | 10/2002 | Schmidt et al. | |
| 6,555,651 B2 | 4/2003 | Stern et al. | |
| 6,563,015 B1 | 5/2003 | Stern et al. | |
| 6,660,843 B1 | 12/2003 | Feige et al. | |
| 6,753,150 B2 | 6/2004 | Schmidt et al. | |
| 6,790,443 B2 | 9/2004 | Stern et al. | |
| 6,825,164 B1 | 11/2004 | Stern et al. | |
| 6,908,741 B1 | 6/2005 | Shahbaz | |
| 7,166,707 B2 | 1/2007 | Feige | |
| 7,217,799 B2 | 5/2007 | Raitano et al. | |
| 7,241,733 B2 * | 7/2007 | Heavner et al. ............ | 514/2 |
| 7,393,662 B2 * | 7/2008 | Heavner et al. ............ | 435/69.7 |
| 2001/0053357 A1 | 12/2001 | Stern et al. | |
| 2003/0082749 A1 * | 5/2003 | Sun et al. ................. | 435/70.21 |
| 2003/0170626 A1 | 9/2003 | Raitano et al. | |
| 2004/0142391 A1 | 7/2004 | Schmidt et al. | |
| 2004/0210042 A1 | 10/2004 | Tsuchida | |
| 2005/0026811 A1 | 2/2005 | Mjalli et al. | |
| 2005/0033017 A1 | 2/2005 | Yamamoto et al. | |
| 2005/0129682 A1 | 6/2005 | Schmidt et al. | |

FOREIGN PATENT DOCUMENTS

| | | |
|---|---|---|
| WO | WO 93/04086 A1 | 3/1993 |
| WO | WO 97/39121 A1 | 10/1997 |
| WO | WO 97/39125 A1 | 10/1997 |
| WO | WO 98/22138 A1 | 5/1998 |
| WO | WO 99/07402 A1 | 2/1999 |
| WO | WO 99/18987 A1 | 4/1999 |
| WO | WO 99/54485 A1 | 10/1999 |
| WO | WO 01/92210 A1 | 12/2001 |
| WO | WO 01/92892 A2 | 12/2001 |
| WO | WO 02/070667 A2 | 9/2002 |
| WO | WO 03/084477 A2 | 10/2003 |
| WO | WO 2004/002417 A2 | 1/2004 |
| WO | WO 2004/002424 A2 | 1/2004 |
| WO | WO2004/016229 A2 | 2/2004 |
| WO | WO 2005/032460 A2 | 4/2005 |
| WO | WO 2006/017643 A1 | 2/2006 |

OTHER PUBLICATIONS

Xu et al. In vitro characterization of five humanized OKT3 effector function variant antibodies. Cell Immunol. Feb. 25, 2000;200(1):16-26.*
R&D Systems, Inc. "Recombinant Human Rage/Fc Chimera," Catalog No. 1145-RG, Internet Citation May 3, 2004.
Rouhiainen, et al., "Regulation of monocyte migration by amphoterin (HMGB1)," Blood, 104(4): 1174-1182 (2004).
Huttunen, et al., "Receptor for Advanced Glycation End Products-binding COOH-terminal Motif of Amphoterin Inhibits Invasive Migration and Metastasis," Cancer Research, 62: 4805-4811 (2002).
Supplemental EP Search Report dated Dec. 18, 2008.
Aalberse, et al., "IgG4 breaking the rules," Immunology, 105: 9-19 (2002).
Deane, et al., "RAGE mediates amyloid-β peptide transport across the blood-brain barrier and accumulation in brain," Nature Medicine, 9: 907-913 (2003).
Hofmann, et al., "RAGE Mediates a Novel Proinflammatory Axis: A Central Cell Surface Receptor for S100 Calgranulin Polypeptides," Cell, vol. 97: 889-901 (1999).
Hori, et al., "The Receptor for Advanced Glycation End Products (RAGE) Is a Cellular Binding Site for Amphoterin," The Journal of Biological Chemistry, 270(43): 25752-25761 (1995).
Kislinger, et al., "N$^\epsilon$-9Carboxymethyl)Lysine Adducts of Proteins Are Ligands for Receptor for Advanced Glycation End Products that Activate Cell Signaling Pathways and Modulate Gene Expression," The Journal of Biological Chemistry, 274(44): 31740-31749 (1999).
Park, et al., "Suppression of accelerated diabetic atherosclerosis by the soluble receptor for advanced glycation endproducts," Nature Medicine: 4(9): 1025-1031 (1998).
Scaffidi, et al., "Release of chromatin protein HMGB1 by necrotic cells triggers inflammation," Nature, 418: 191-195 (2002).
Schmidt, et al., "Isolation and Characterization of Two Binding Proteins for Advanced Glycosylation End Products from Bovine Lung Which are Present on the Endothelial Cell Surface," The Journal of Biological Chemistry, 267(21): 14987-14997 (1992).
Schmidt, et al., "The dark site of glucose," Nature Medicine, 1(10): 1002-1004 (1995).
Taguchi, et al., "Blocade of RAGE-amphoterin signaling suppresses tumour growth and metastases," Nature, 405: 354-260 (2000).
Wang, et al., "HMG-1 as a Late Mediator of Endotoxin Lathality in Mice," Science, 285: 248-251 (1999).

*Primary Examiner* — Daniel E Kolker
*Assistant Examiner* — Gregory S Emch
(74) *Attorney, Agent, or Firm* — Kirk Baumeister

(57) ABSTRACT

Mammalian sRAGE mimetibody polypeptides and nucleic acids are disclosed. Methods of utilizing the polypeptides to reduce or inhibit the binding of RAGE and its ligands and to treat RAGE-related diseases are also disclosed.

5 Claims, 11 Drawing Sheets

OTHER PUBLICATIONS

Yan, et al., "RAGE and amyloid-β peptide neurotoxicity in Alzheimer's disease," Nature, 382: 685-691 (1996).

Renard, et al., "Recombinant Advanced Glycation End Product Receptor Pharmacokinetics in Normal and Diabetic rates," Molecular Pharmacology, 52: 54-62 (1997).

Lotze, et al., "Dealing with death: HMGB1 as a novel target for cancer therapy," Current Opinion in Investigational Drugs, 4: 1405-1409 (2003).

Zhang, et al., "Targeting of functional antibody-CD59 fusion proteins to a cell surface," The Journal of Clinical Investigation, 103(1): 55-61 (1999).

Shin, et al., "Transferrin-antibody fusion proteins are effective in brain targeting," Proceedings of the National Academy of Sciences USA, 92: 2820-2824 (1995).

Lilley, et al, "Recombinant single-chain antibody peptide conjugates expressed in *Escherichia coli* for the rapid diagnosis of HIV," Journal of Immunological Methods, 171: 211-226 (1994).

Koyama, et al., "RAGE and soluble RAGE: Potential therapeutic targets for cardiovascular diseases," Molecular Medicine, 13 (11-12): 625-635 (2007).

Yan, et al., "Two-amino acid molecular switch in an epithelial morphogen that regulates binding to two distinct receptors," Science, 290: 523-527 (2000).

W.E. Paul, Fundamental Immunology, $3^{rd}$ ed., 292-295 (1993).

Rudikoff, et al., "Single amino acid substitution altering antigen-binding specificity," Proceedings of the National PCT International Search Report dated Jul. 12, 2006.

* cited by examiner

Binding of V-domain IgG1 to AGE sRAGE Mimetibody inhibition of AGE binding to U937 cells

SRAGE MIMETIBODY, COMPOSITIONS, METHODS AND USES

CROSS REFERENCE TO RELATED APPLICATION

This application is a divisional of U.S. application Ser. No. 11/235,776, filed 27 Sep. 2005, currently pending, which claims priority to U.S. Provisional Application Ser. No. 60/613,247, filed 27 Sep. 2004. The entire contents of each of the foregoing are incorporated herein by reference.

FIELD OF THE INVENTION

The present invention relates to mammalian sRAGE mimetibodies and their use as therapeutics.

BACKGROUND OF THE INVENTION

The Receptor for Advanced Glycated Endproducts (RAGE) is a member of the immunoglobulin superfamily of cell-surface molecules. It was originally identified and characterized as a cellular receptor for glucose (aldose sugar)-modified proteins or Advanced Glycated Endproducts (AGE) (Schmidt et al., J. Biol. Chem. 267: 14987-14997, (1992); Neeper et al., J. Biol. Chem. 267: 14998-15004, (1992)). AGE have been implicated in a variety of disorders associated with diabetes and aging (reviewed in Schmidt et al., Nature Med. 1: 1002-1004, (1995)). Binding of AGE to RAGE induces inflammatory responses in blood vessel walls, which can trigger or aggravate the pathogenesis of macro- or micro-angiopathy.

RAGE has also been reported to interact with other ligands, including amphoterin, a matrix-associated polypeptide that promotes outgrowth of cultured cortical neurons derived from developing brain (Hori et al., J. Biol. Chem. 270: 25752-25761, (1995)). Amphoterin, also known in the literature as high mobility group B1 (HMGB1), has been shown to contribute to a variety of disease states including cancer, inflammatory conditions and sepsis. See Lotze and DeMarco, Curr. Opin. Investig. Drugs 4: 1405-1409 (2003); Scaffidi et al., Nature 418: 191-195 (2002); and Wang et al., Science 285: 248-251 (1999). The expression of RAGE is markedly enhanced and co-localizes with that of amphoterin at the leading edge of advancing neurites, which indicates a potential contribution to cellular migration and in pathologies such as tumor invasion. It has been reported that either anti-RAGE F(ab')$_2$ or soluble RAGE inhibited neurite outgrowth on amphoterin-coated matrices (Taguchi et al., Nature 405: 354-360, (2000)). Soluble RAGE (sRAGE) is the extracellular domain of the receptor. In addition, blockade of RAGE-amphoterin binding decreased growth and metastases of both implanted tumors and tumors developing spontaneously in susceptible mice, Id.

RAGE has also been identified as a receptor on neurons and microglia for β-amyloid, a polypeptide linked to the pathogenesis of neuronal toxicity and death in Alzheimer's disease (Yan et al., Nature 382: 685-691 (1996)). Expression of RAGE is particularly increased in neurons close to deposits of β-amyloid peptide and to neurofibrillary tangles. In mice, RAGE mediates the transport of human β-amyloid-40 and -42 across the blood-brain barrier (Deane et al., Nature Med. 9: 907-913 (2003)). Inhibition of the RAGE-ligand interaction, either by anti-RAGE IgG or soluble RAGE, neither of which is transported across the blood-brain barrier, suppressed the accumulation of β-amyloid in brain parenchyma in a mouse model of Alzheimer's disease, Id.

RAGE is also a central cell surface receptor for S100A2 and related members of the S100/calgranulins superfamily (Hofmann et al., Cell 97: 889-901 (1999)). Interaction of S100A2 and cellular RAGE on endothelium, mononuclear phagocytes and lymphocytes triggers cellular activation and generation of key proinflammatory mediators. In murine models, blockade of S100A2/RAGE quenched delayed-type hypersensitivity and inflammatory colitis by arresting activation of central signaling pathways and expression of inflammatory gene mediators, Id.

Studies have also shown that binding of RAGE by a ligand triggers activation of key cell signaling pathways, such as p21(ras), MAP kinases, NF-κb, and cdc42/rac thereby reprogramming cellular properties. For example, upon ligand binding, RAGE initiates a signaling cascade that results in the translocation of NF-κb to the nucleus and increased expression of adhesion molecules, procoagulant molecules and inflammatory proteins (Kislinger et al., J. Biol. Chem. 274: 31740-31749 (1999)).

Studies have indicated that RAGE interacts with various molecules implicated in homeostasis, development, inflammation, and certain diseases such as Type 2 diabetes and Alzheimer's disease. Accordingly, it would generally be desirable to block or otherwise inhibit these interactions, when associated with a disease state, to treat or prevent the associated pathologies.

sRAGE has been shown to be efficacious in animal disease models for atherosclerosis, tumor growth and metastasis, colitis, delayed-type hypersensitivity, experimental allergic encephalomyelitis, and Alzheimers disease (Park et al., Nature Med. 4: 1025-1031 (1998); Taguchi et al., supra; Hofmann et al., supra; Yan et al., supra) and can be purified or expressed recombinantly. sRAGE lacks the transmembrane and extracellular domains of full-length RAGE and has three immunoglobulin-like regions: an N-terminal region most similar to an immunoglobulin variable domain (V domain) followed by two regions resembling immunoglobulin constant regions (C domains).

SRAGE has been used extensively in vitro and in vivo to study RAGE-ligand interactions. However, the half-life of sRAGE in rats is 24 hours and therefore sRAGE itself is impractical as a therapeutic for disease. Further, an anti-RAGE IgG would have to bind and inhibit large amounts of RAGE normally expressed in tissues such as lung and may induce death of normal cells. Thus, a need exists for a modified sRAGE that will overcome the short half-life while retaining the AGE binding function of RAGE.

SUMMARY OF THE INVENTION

Figure 1A:
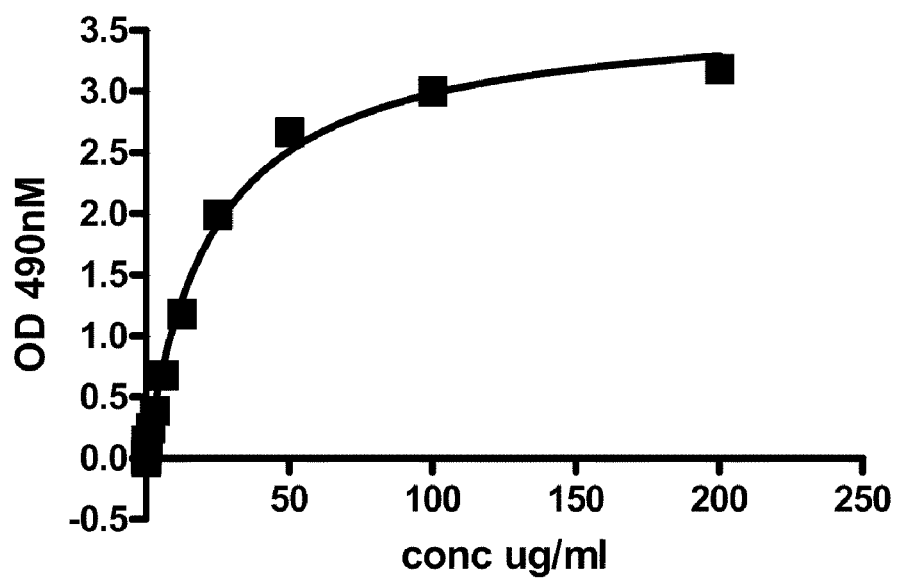
FIGS. 1A to 1E show sRAGE mimetibody binding to AGEs. The mimetibodies tested include 1A: V in IgG1 with C220A and L234A/L235A mutations (V-G1)(SEQ ID NO: 5); 1B: V-C-C in IgG1 with C220A and L234A/L235A mutations (VCC-G1)(SEQ ID NO: 3); 1C: V in IgG4 with S228P and P234A, L235A mutations (V-G4)(SEQ ID NO: 13); 1D: V-C in IgG4 with S228P and P234A/L235A mutations (VC-G4)(SEQ ID NO: 11); and 1E: V-C-C in IgG4 with S228P and P234A/L235A mutations (VCC-G4) (SEQ ID NO: 9).
Figure 1B:
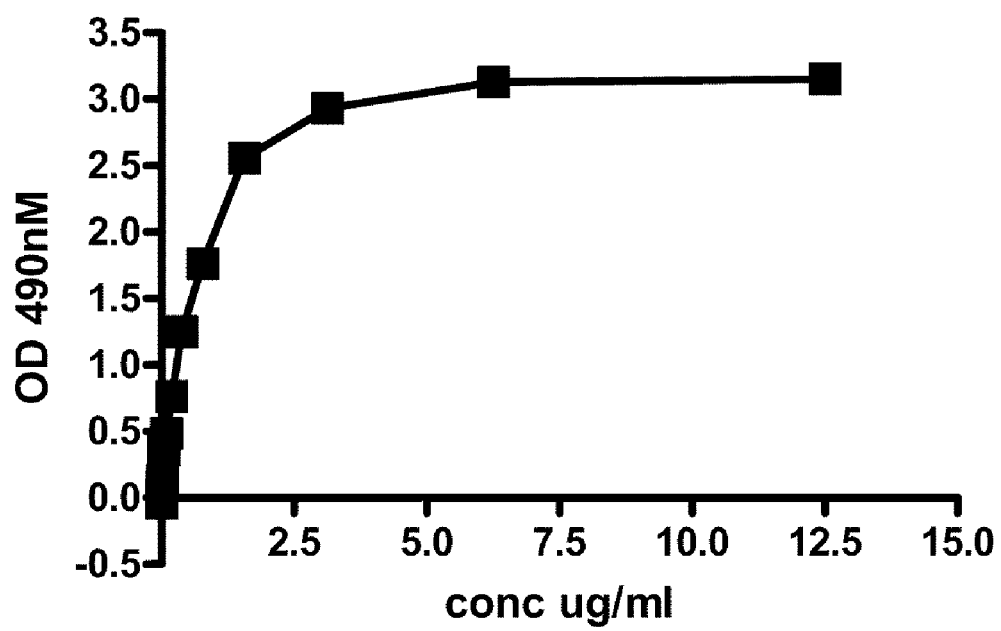
Figure 1C:
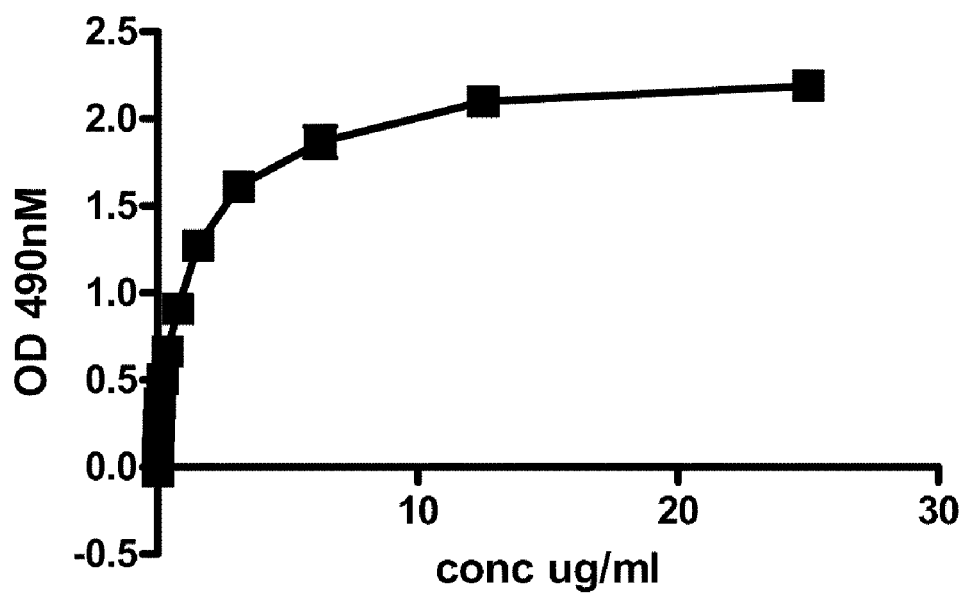
Figure 1D:
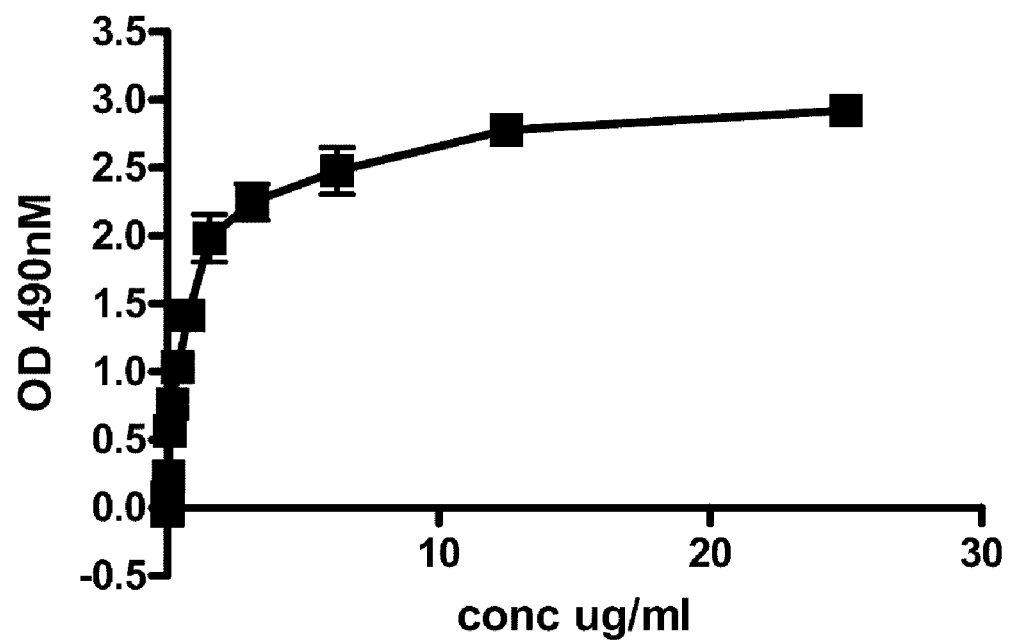
Figure 1E:
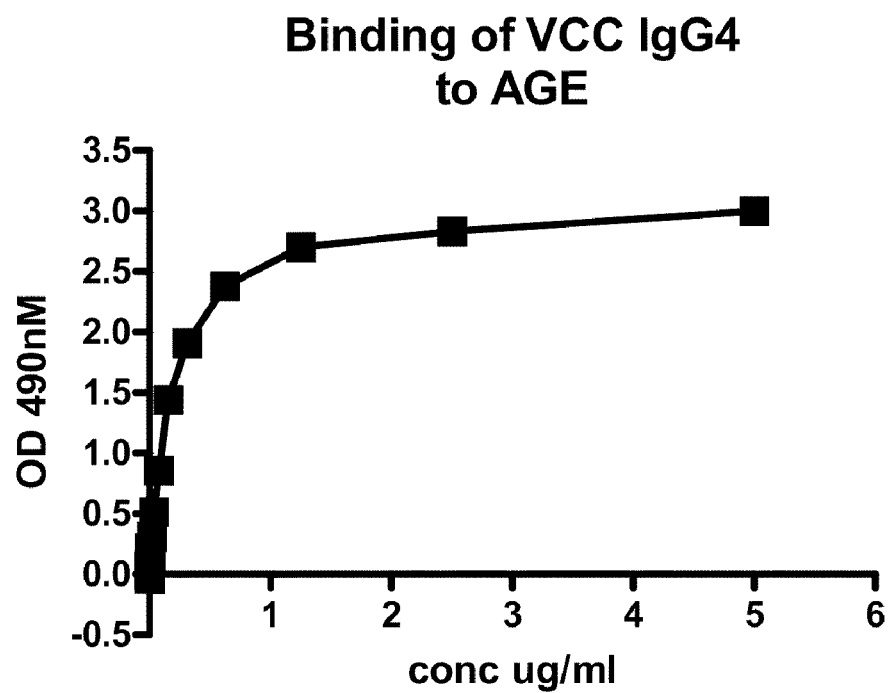

One aspect of the invention is a polypeptide having the generic formula (II):

$$(Rg\text{-}Lk\text{-}V2\text{-}Hg\text{-}C_H2\text{-}C_H3)_{(t)} \quad\quad (II)$$

where Rg is a mammalian sRAGE sequence, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10.

Another aspect of the invention is a polypeptide comprising a polypeptide having the sequence shown in SEQ ID NO: 3, 5, 7, 9, 11 or 13.

Another aspect of the invention is a polynucleotide comprising a polynucleotide having the sequence shown in SEQ ID NO: 4, 6, 8, 10, 12 or 14 or a complementary sequence.

Another aspect of the invention is a polynucleotide comprising a polynucleotide encoding the amino acid sequence shown in SEQ ID NO: 3, 5, 7, 9, 11 or 13.

Another aspect of the invention is a method of modifying the biological activity of RAGE in a mammal comprising administering an sRAGE mimetibody composition to the mammal.

Another aspect of the invention is a method of reducing the symptoms of, or treating at least one RAGE-related condition or disorder, comprising administering an sRAGE mimetibody composition to a patient in need thereof.

DETAILED DESCRIPTION OF THE INVENTION

All publications, including but not limited to patents and patent applications, cited in this specification are herein incorporated by reference as though fully set forth. Single letter amino acid codes are used herein as understood by those skilled in the art. Numbering of amino acid residues in immunoglobulin constant regions is based on residue one being the N-terminal amino acid in a wild type IgG1 or IgG4 Fc domain.

The present invention provides polypeptides having the properties and activities of mammalian sRAGE wherein the polypeptides also mimic different types of immunoglobulin molecules such as IgA, IgD, IgE, IgG, or IgM, and any subclass thereof, such as IgA1, IgA2, IgG1, IgG2, IgG3 or IgG4, or combinations thereof, hereinafter referred to as "sRAGE mimetibodies." The invention also provides nucleic acids encoding sRAGE mimetibodies, vectors containing these nucleic acids, host cells, compositions and methods of making and using sRAGE mimetibodies.

Mimetibody Polypeptides and Compositions

The present invention generally relates to mimetibody polypeptides having the generic formula (I):

$$(Pep\text{-}Lk\text{-}V2\text{-}Hg\text{-}C_H2\text{-}C_H3)_{(t)} \quad\quad (I)$$

where Pep is a polypeptide having a desired biological property, Lk is a polypeptide or chemical linkage, V2 is a portion of a C-terminus of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10.

More particularly, the present invention relates to sRAGE mimetibody polypeptides that are capable of blocking or reducing interactions between RAGE and its respective ligands such as AGE, amphoterin, S100/calgranulin and β-amyloid. The polypeptides have the generic formula (II):

$$(Rg\text{-}Lk\text{-}V2\text{-}Hg\text{-}C_H2\text{-}C_H3)_{(t)} \quad\quad (II)$$

where Rg is a mammalian sRAGE sequence, Lk is a polypeptide or chemical linkage, V2 is a portion of a C-terminus of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10.

As used herein, "soluble RAGE" or "sRAGE" encompasses RAGE-derived polypeptides that lack the transmembrane and intracellular regions associated with full-length RAGE. An exemplary mammalian sRAGE polypeptide is the extracellular domain of human sRAGE having the amino acid sequence shown in SEQ ID NO: 1. It is readily understood by those skilled in the art that sRAGE polypeptides can also include biologically active fragments of SEQ ID NO: 1, amino acid sequences that are substantially homologous to SEQ ID NO: 1 as well as polypeptides that can mimic the binding activity of sRAGE. It will also be understood by those skilled in the art that the mammalian sRAGE polypeptides useful in the present invention can include a native N-terminal leader sequence (amino acids 1-30 of SEQ ID NO: 1) or other leader sequence to facilitate excretion of the polypeptides of the invention from their production cell line.

The term "biologically active fragment" as used herein, refers to portions of sRAGE polypeptides that can specifically bind to an sRAGE ligand. Examples of biologically active fragments of sRAGE include, but are not limited to, one or more of the Ig-like domains, such as the single V domain (amino acids 31-106 of SEQ ID NO: 1), the V domain and a C domain (amino acids 31-215 of SEQ ID NO: 1), or the V domain and both C domains (amino acids 31-308 of SEQ ID NO: 1).

The term "substantially homologous" in the context of polypeptides, refers to two amino acid sequences which, when optimally aligned, are at least about 80% homologous or at least about 85% homoglous or at least about 90% homoglous or at least about 95% homologous. Alignment for purposes of determining percent amino acid homology can be achieved in various ways that are within the skill in the art, for example, by using the default settings for the AlignX component of Vector NTI Suite 8.0 (Informax, Frederick, Md.) or publicly available computer software such as BLAST (Altschul et al., J. Mol. Biol. 215: 403-410 (1990)). A polypeptide sequence substantially homologous to SEQ ID NO: 1 has at least one amino acid substitution, deletion or insertion.

In the polypeptides of the invention, the linker portion (Lk) provides structural flexibility by allowing the mimetibody to have alternative orientations and binding properties. Exemplary linkers include non-peptide chemical linkages or one to 20 amino acids linked by peptide bonds, wherein the amino acids are selected from the 20 naturally occurring amino acids. The linker portion can include a majority of amino acids that are sterically unhindered, such as glycine, alanine and serine and include GS, poly GS, GGGS (SEQ ID NO: 32), polymers of GGGS and GSGGGS (SEQ ID NO: 33) or any combination thereof. Other exemplary linkers within the scope of the invention may be longer than 20 residues and may include residues other than glycine, alanine and serine.

In the polypeptides of the invention, V2 is a portion of a C-terminal domain of an immunoglobulin variable region such as a heavy chain variable region. An exemplary V2 amino acid sequence is GTLVTVSS (SEQ ID NO: 16).

In the polypeptides of the invention, Hg is a portion of the hinge domain of an immunoglobulin variable region such as a heavy chain variable region. Exemplary H amino acid sequences include EPKSCDKTHTCPPCP (SEQ ID NO: 17), EPKSADKTHTCPPCP (SEQ ID NO: 18), ESKYGPPCPSCP (SEQ ID NO: 19), ESKYGPPCPPCP (SEQ ID NO: 20) and CPPCP (SEQ ID NO: 21).

In the polypeptides of the invention, $C_H2$ is an immunoglobulin heavy chain $C_H2$ constant region. Exemplary $C_H2$ amino acid sequences include:

(SEQ ID NO: 22)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK, (SEQ ID NO: 23)
APEAAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK, (SEQ ID NO: 25)
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK
and (SEQ ID NO: 26)
APEAAGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK.

In the polypeptides of the invention, $C_H3$ is an immunoglobulin heavy chain $C_H3$ constant region. Exemplary $C_H3$ amino acid sequences include: GQPREPQVYTLPPSRDELTKNQVSLTCLVKGFYPSDIAVEWESNGQPENNYKTTPPVLDSDGSFFLYS KLTVDKSRWQQGNVFSCSVMHEALHNHYTQKSLSLSPGK (SEQ ID NO: 24) and GQPREPQVYTLPPSQEEMTKNQVSLTCLVKGFYPSDIAVEWESNGQPENNYKTTPPVLDSDGSFFLYS RLTVDKSRWQEGNVFSCSVMHEALHNHYTQKSLSLSLGK (SEQ ID NO: 27). It will be recognized by those skilled in the art that the $C_H3$ region of the polypeptides of the invention may have its C-terminal amino acid cleaved off when expressed in certain recombinant systems.

In the polypeptides of the invention, the FcRn scavenger receptor binding site of the immunoglobulin molecules is preserved at the junction of the $C_H2$ and $C_H3$ region. Since FcRn binding enables the return of pinocytosed immunoglobulin back to the extracellular space, it is expected that the half-life of sRAGE mimetibodies will be significantly extended relative to sRAGE.

The polypeptides of the invention can optionally comprise, at their N-terminal, a portion of an N-terminus of an immunoglobulin variable region, designated V1 as shown in Formula III. Exemplary V1 amino acid sequences include QIQ or QVQ.

$$(V1-Rg-Lk-V2-Hg-C_H2-C_H3)_{(t)} \quad (III)$$

In one embodiment of the polypeptides of the invention, the monomeric structure ($Rg-Lk-V2-Hg-C_H2-C_H3$) can be linked to other monomers non-covalently or by covalent linkage, such as, but not limited to, a Cys-Cys disulfide bond. It is thought that this structure will allow stable dimerization of sRAGE and increase its affinity to RAGE ligands.

Another embodiment of the present invention is a polypeptide comprising a polypeptide according to formula (II) where Rg is a single copy of the RAGE full-length extracellular domain (SEQ ID NO: 1), V2 is a J region of a naturally occurring IgG (SEQ ID NO: 16), Hg is a complete IgG1 hinge region with a Cys220Ala (C220A) substitution (SEQ ID NO: 18) and $C_H2$ and $C_H3$ are of the IgG1 isotype subclass with Leu234Ala and Leu235Ala substitutions (L234A/L235A) (SEQ ID NO: 28). The complete polypeptide sequence of this embodiment is shown in SEQ ID NO: 3.

Another embodiment of the present invention is a polypeptide comprising a polypeptide according to formula (II) where Rg is a single copy of the V domain of the RAGE full-length extracellular domain (residues 31 to 106 of SEQ ID NO: 1), V2 is a J region of a naturally occurring IgG (SEQ ID NO: 16), Hg is a complete IgG1 hinge region with a C220A substitution (SEQ ID NO: 18) and $C_H2$ and $C_H3$ are of the IgG1 isotype subclass with L234A/L235A substitutions (SEQ ID NO: 28). The complete polypeptide sequence of this embodiment is shown in SEQ ID NO: 5.

Another embodiment of the present invention is a polypeptide comprising a polypeptide according to formula (II) where Rg is a single copy of the RAGE full-length extracellular domain (SEQ ID NO: 1), V2 is a J region of a naturally occurring IgG (SEQ ID NO: 16), Hg is the complete IgG4 hinge region (SEQ ID NO: 19) and $C_H2$ and $C_H3$ are of the IgG4 isotype subclass (SEQ ID NO: 29). The complete polypeptide sequence of this embodiment is shown in SEQ ID NO: 7.

IgG1 and IgG4 subclasses differ in the number of cysteines in the hinge region. Like the IgG1 subclass, there are two cysteines in the IgG4 hinge that participate in the disulfide bonding between heavy chains. However, the cysteine in IgG1 hinge that is normally involved in disulfide bonding to the light chain is absent in the IgG4 hinge. Therefore, the IgG4 hinge is less flexible than the IgG1 hinge.

In addition, the two isotypes differ in their ability to mediate complement dependent cytotoxicity (CDC) and antibody-dependent cellular cytotoxicity (ADCC). CDC is the lysing of a target in the presence of complement. The complement activation pathway is initiated by the binding of the first component of the complement system (C1q) to a molecule complexed with a cognate antigen. IgG1 is a strong inducer of the complement cascade and subsequent CDC activity, while IgG4 has little complement-inducing activity.

ADCC is a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The IgG1 subclass binds with high affinity to the Fc receptor and contributes to ADCC while IgG4 binds only weakly. The relative inability of IgG4 to activate effector functions is desirable since delivery of the mimetibody to cells without cell killing is possible.

Furthermore, the binding site for the FcRn scavenger receptor is present in IgG4 and IgG1 isotypes and both have similar binding characteristics. Therefore, the pharmacokinetics of the IgG1 and IgG4 mimetibodies of the invention are expected to be similar.

The hinge-$C_H2$-$C_H3$ portion of the immunoglobulin region (Hg-$C_H2$-$C_H3$) may also be extensively modified to form variants in accordance with the invention. For example, one or more native sites that provide structural features or functional activity not required by the mimetibody molecules could be removed. These sites may be removed by, for example, substituting or deleting residues, inserting residues into the site, or truncating portions containing the site. Exemplary Hg-$C_H2$-$C_H3$ variants are discussed below.

1. Sites involved in disulfide bond formation can be removed by deletion or substitution with other amino acids in the mimetibodies of the invention. Typically, the cysteine residues present in these motifs are removed or substituted. Removal of these sites may avoid disulfide bonding with other cysteine-containing proteins present in the mimetibody-producing host cell or intra-heavy chain disulfide bonding in IgG4-based constructs while still allowing for a dimeric CH3-CH2-hinge domain that is held together non-covalently.

Most IgG type antibodies, such as IgG1, are homodimeric molecules made up of two identical heavy (H) chains and two identical light (L) chains, typically abbreviated $H_2L_2$. Thus, these molecules are generally bivalent with respect to antigen binding, i.e., both antigen binding (Fab) arms of the IgG molecule have identical binding specificity.

IgG4 isotype heavy chains contain a CPSC (SEQ ID NO: 15) motif in their hinge regions capable of forming either inter- or intra-heavy chain disulfide bonds, i.e., the two Cys residues in the CPSC motif may disulfide bond with the corresponding Cys residues in the other H chain (inter) or the two Cys residues within a given CPSC motif may disulfide bond with each other (intra). It is believed that in vivo isomerase enzymes are capable of converting inter-heavy chain bonds of IgG4 molecules to intra-heavy chain bonds and vice versa (Aalberse and Schuurman, *Immunology* 105, 9-19 (2002)). Accordingly, since the HL pairs in those IgG4 molecules with intra-heavy chain bonds in the hinge region are not covalently associated with each other, they may dissociate into HL monomers that then reassociate with HL monomers derived from other IgG4 molecules forming bispecific, heterodimeric IgG4 molecules. In a bispecific IgG antibody the two Fabs of the antibody molecule differ in the epitopes that they bind. Substituting Ser228 in the hinge region of IgG4 with Pro results in "IgG1-like behavior," i.e., the molecules form stable disulfide bonds between heavy chains and therefore, are not susceptible to HL exchange with other IgG4 molecules.

2. The H-$C_H2$-$C_H3$ can be modified to make the mimetibodies of the invention more compatible with a selected host cell. For example, when a mimetibody of the invention is expressed recombinantly in a bacterial cell such as *E. coli*, the Pro-Ala sequence in the hinge may be removed to prevent digestion by the *E coli* enzyme proline iminopeptidase.

3. A portion of the hinge region can be deleted or substituted with other amino acids in the mimetibodies of the invention to prevent heterogeneity in the products expressed in a selected host cell.

4. One or more glycosylation sites can be removed in the mimetibodies of the invention. Residues that are typically glycosylated (e.g., Asn) may confer an Fc-dependent, cell-mediated cytolytic activity to the mimetibody. Such residues may be deleted or substituted with residues that are not glycosylated such as Ala.

5. Sites involved in interaction with complement, such as the C1q binding site, are removed in the mimetibodies of the invention.

6. Sites can be removed that affect binding to Fc receptors other than a FcRn salvage receptor in the mimetibodies of the invention. For example, the Fc receptors involved in ADCC activity can be removed in the mimetibodies of the invention. For example, mutation of Leu234/Leu235 in the hinge region of IgG1 to L234A/L235A or Phe234/Leu235 in the hinge region of IgG4 to P234A/L235A minimizes FcR binding and reduces the ability of the immunoglobulin to mediate complement dependent cytotoxicity and ADCC.

One embodiment of the present invention is an sRAGE mimetibody according to formula (II) where the Hg-$C_H2$-$C_H3$ is from the IgG4 subclass (SEQ ID NO: 30) and contains a Ser228Pro (S228P) substitution and P234A/L235A mutations (SEQ ID NO: 31). The complete polypeptide sequences of exemplary sRAGE mimetibody polypeptides having these mutations and the (V-C-C), (V-C) and (V) domains of sRAGE, are shown respectively in SEQ ID NOs: 9, 11 and 13. These mimetibody constructs are expected be a homogeneous and stable population that does not trigger FcR-mediated effector functions. The substitution and mutations shown here are exemplary; Hg-$C_H2$-$C_H3$ domains within the scope of this invention may include other substitutions, mutations and/or deletions.

As mentioned above, the amino acid sequences of specific examples of mimetibodies of the invention are shown in SEQ ID NOs: 3, 5, 7, 9, 11 and 13. The characterstics of these constructs are shown in Table 1 (n.a.=not applicable).

TABLE 1

Exemplary mimetibody constructs

| SEQ ID NO: | SRAGE domains | Ig isotype | C220A | S228P | L234A/ L235A | P234A/ L235A |
|---|---|---|---|---|---|---|
| 3 | V-C-C | IgG1 | Yes | n.a. | Yes | n.a. |
| 5 | V | IgG1 | Yes | n.a. | Yes | n.a. |
| 7 | V-C-C | IgG4 | n.a. | No | n.a. | No |
| 9 | V-C-C | IgG4 | n.a. | Yes | n.a. | Yes |
| 11 | V-C | IgG4 | n.a. | Yes | n.a. | Yes |
| 13 | V | IgG4 | n.a. | Yes | n.a. | Yes |

The present invention includes sRAGE mimetibodies that are capable of blocking or reducing interactions between RAGE and at least one of its ligands. Embodiments of the invention include sRAGE mimetibodies that specifically bind to AGEs, amphoterin, S100/calgranulin or β-amyloid or any combination thereof. The mimetibodies of the present invention can bind RAGE ligands with a wide range of affinities. Exemplary sRAGE mimetibodies bind at least one RAGE ligand with high affinity. For example, an sRAGE mimetibody can bind at least one of AGEs, amphoterin, S100/calgranulin, β-amyloid or any combination thereof with a Kd equal to or less than about $10^{-7}$M, $10^{-8}$, $10^{-9}$, $10^{-10}$, $10^{-11}$ or $10^{-12}$M.

The affinity of an sRAGE mimetibody for a specific RAGE ligand can be determined experimentally using any suitable method, for example, methods using Biacore or KinExA instrumentation, ELISA and competitive binding assays. sRAGE mimetibodies having specific ligand binding capabilities can be selected from libraries of sRAGE variants or sRAGE fragments by techniques known to those skilled in the art.

The sRAGE mimetibodies of the present invention are useful in treating disorders or symptoms resulting from abnormal receptor activation of RAGE triggered by at least one ligand's binding. As described previously, the association of RAGE and its ligands has been implicated in a number of pathological conditions, such as but not limited to, Types 1 and 2 diabetes and Alzheimer's disease. Accordingly, another aspect of the present invention is pharmaceutical compositions comprising at least one sRAGE mimetibody and a pharmaceutically acceptable carrier or diluent known in the art. The carrier or diluent can be a solution, suspension, emulsion, colloid or powder.

An sRAGE mimetibody of the invention is formulated as a pharmaceutical composition in a therapeutically or prophylactically effective amount. The term "effective amount" generally refers to the quantities of mimetibody necessary for effective therapy, i.e., the partial or complete alleviation of the symptom or disorder for which treatment was sought. Included within the definition of effective therapy are prophylactic treatments intended to reduce the likelihood of onset of the above-described symptoms or disorders.

The composition can optionally comprise at least one further compound, protein or composition useful for treating the disease states discussed below. For example, combination with insulin, metformin, sulfonylureas or PPAR-γ agonists are contemplated in the treatment of Type 2 diabetes. Further, combination with anti-inflammatory agents to treat inflammatory disorders and combination with chemotherapy agents to treat cancer are also contemplated.

Nucleic Acids, Vectors and Cell Lines

Another aspect of the present invention is isolated nucleic acid molecules comprising, complementary to or having significant identity with a polynucleotide encoding at least one sRAGE mimetibody. Other aspects of the present invention include recombinant vectors comprising at least one isolated sRAGE mimetibody encoding nucleic acid molecule and cell lines and organisms that are capable of expressing the nucleic acid molecules. The nucleic acids, expression vectors and cell lines may generally be used to produce the mimetibody of the invention.

In one embodiment, the nucleic acid compositions of the invention encode polypeptides having amino acid sequences identical to or substantially homologous to any one of SEQ ID NOs: 3, 5, 7, 9, 11 or 13. Exemplary nucleic acid sequences that encode the polypeptide sequences shown in SEQ ID NOs: 3, 5, 7, 9, 11 and 13 are shown in SEQ ID NOs: 4, 6, 8, 10, 12 and 14, respectively. Also provided are substantially similar nucleic acid sequences and allelic variations of the above-described nucleic acids.

The term "substantially similar" in the nucleic acid context, means that the segments, or their complementary strands, when properly aligned, with the appropriate nucleotide insertions or deletions, are identical in at least 60% or at least about 70% or at least about 80% or at least about 90% or at least about 95-98% of the nucleotides. Values for % identity can be obtained from nucleotide sequence alignments generated using the default settings for the AlignX component of Vector NTI Suite 8.0 (Informax, Frederick Md.).

Typically, the nucleic acids of the present invention are used in expression vectors for the preparation of the sRAGE mimetibody polypeptides of the invention. Vectors within the scope of the invention provide necessary elements for eukaryotic expression, including viral promoter driven vectors, such as CMV promoter driven vectors, e.g., pcDNA3.1, pCEP4 and their derivatives, Baculovirus expression vectors, Drosophila expression vectors and expression vectors that are driven by mammalian gene promoters, such as human Ig gene promoters. Other examples include prokaryotic expression vectors, such as T7 promoter driven vectors, e.g., pET41, lactose promoter driven vectors and arabinose gene promoter driven vectors.

The present invention also relates to cell lines expressing sRAGE mimetibodies. The host cells can be prokaryotic or eukaryotic cells. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells, or any derivative thereof. Most preferably, the host cells are HEK293, NS0, SP2/0 or CHO cells. The cell lines of the present invention may stably express at least one sRAGE mimetibody. The cell lines may be generated by stable or transient transfection procedures that are well known in the art.

The present invention further provides methods for expressing at least one sRAGE mimetibody comprising culturing the cell lines under conditions wherein the sRAGE mimetibody is expressed in detectable or recoverable amounts. The present invention also provides methods for generating at least one sRAGE mimetibody comprising translating the sRAGE mimetibody encoding nucleic acids under conditions in vitro or in situ, such that the sRAGE mimetibody is expressed in detectable or recoverable amounts. The present invention also encompasses sRAGE mimetibodies produced by the above methods.

An sRAGE mimetibody can be recovered and purified by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylatpatite chromatography and lectin chromatography. High performance liquid chroatography (HPLC) can also be employed for purification.

Methods of Use

The sRAGE mimetibodies are useful as, inter alia, research reagents and therapeutic agents. In one aspect, the present invention relates to a method of modifying the biological activities of RAGE comprising providing at least one sRAGE mimetibody to a mammal in need thereof. The sRAGE mimetibody may decrease or inhibit RAGE-activated cell signaling cascades, such as but not limited to the NF-κb pathway. The sRAGE mimetibody of the invention can thus diminish the increased expression of adhesion molecules, procoagulant molecules and inflammatory proteins due to RAGE-initiated NF-κb translocation into the nucleus. In particular, the sRAGE mimetibody may function as an antagonist of RAGE. The term "antagonist" is used in the broadest sense and includes a molecule that is capable of, directly or indirectly, partially or fully counteracting, reducing or inhibiting one or more biological activities of RAGE. Examples of such biological activites of RAGE include its binding to AGEs, amphoterin, S100/calgranulin or □-amyloid, activation of NF-κb, p21(ras), MAP kinases or cdc42/rac as well as other activities known to those skilled in the art.

The present invention further provides methods for reducing the symptoms of, or treating at least one RAGE-related condition or disease comprising administering a therapeutically effective amount of at least one sRAGE mimetibody pharmaceutical composition to a patient in need thereof. As described above, such composition comprises an effective amount of at least one sRAGE mimetibody and a pharmaceutically acceptable carrier or diluent. The effective amount for a given therapy, whether curative or preventative, will generally depend upon may different factors, including means of administration, target site and other medicants administered. Thus, treatment doses will need to be titrated to optimize safety and efficacy.

The conditions and diseases suitable for treatment using the methods of the present invention include but are not limited to, immune disorders, cardiovascular disorders, metabolic diseases, malignant disorders, and neurologic disorders. Non-limiting examples of these conditions or disorders are Types 1 and 2 diabetes, Alzheimer's disease, atherosclerosis, tumor growth and metastasis, inflammation, colitis, delayed type hypersensititvity, multiple sclerosis and aging related disorders such as oxidant stress. These methods can optionally further comprise co-administration or combination therapies with any standard therapy used to treat the diseases listed above.

The mode of administration can be any suitable route to deliver the pharmaceutically effective amount of sRAGE mimetibody of the present invention to a host. For example, the sRAGE mimetibody can be delivered via parenteral administration, such as subcutaneous, intramuscular, intradermal, intravenous or intranasal administration, or any other means known in the art.

The present invention is further described with reference to the following examples. These examples are merely to illustrate aspects of the present invention and are not intended as limitations of this invention.

Example 1

Cloning, Expression and Purification of an sRAGE Mimetibody in Mammalian Cells

Human sRAGE encoding cDNA was PCR amplified from human fetal lung 5'-STRETCH Plus cDNA Library (Clontech, Palo Alto, Calif.). The first round amplification was performed using forward primer 5'-GTCCCTGGAAG-GAAGCAGG-3' (SEQ ID NO: 34) and reverse primer 5'-TTTGGTACCCCTCAAGGCCCTCCAG-3' (SEQ ID NO: 35).

A second round nested amplification was necessary to yield sufficient quantities of sRAGE cDNAs. The nested forward primers included an NcoI restriction enzyme recognition site and the nested reverse primers included a KpnI site. Specifically, the V region was amplified using forward primer 5'-TTTCCATGGCAGCCGGAACAGCAG-3' (SEQ ID NO: 36) and reverse primer 5'-TTTGGTACCTCCATTCCTGT-TCATTGCCTGG-3' (SEQ ID NO: 37); and the V-C-C region was amplified using forward primer 5'-TTTCCATGGCAGC-CGGAACAGCAG-3' (SEQ ID NO: 36) and reverse primer 5'-TTTGGTACCGTGGCTGGAATGGGTGGCC-3' (SEQ ID NO: 38).

The amplified PCR products (V region or V-C-C region of sRAGE) were cloned into the NcoI/KpnI site of an intermediate vector using standard cloning procedures. The EcoRI fragment of the assembled intermediate plasmids, containing promoter elements, enhancers and sRAGE encoding sequences were cloned into a mouse Ig gene promoter driven, human IgG1 ΔCH1 Ala/Ala expression vector. Plasmids expressing a V region containing sRAGE mimetibody and a V-C-C containing sRAGE mimetibody were generated.

The sRAGE IgG1 mimetibodies were stably expressed in mouse myeloma cells SP2/0 and purified from the conditioned media using protein A affinity chromatography according to standard procedures.

The sRAGE mimetibodies were also cloned into an IgG4 Ser to Pro, Ala/Ala scaffold. To amplify fragments encoding the V-C and the V-C-C sRAGE mimetibodies, the V-C-C containing plasmid was used as the template. The forward primers included an NheI site, and the reverse primers included a BamHI site. Specifically, the V-C region was amplified using forward primer 5'-TTTGCTAGCGCCAC-CATGGCAGCCGGAACAGCAGTT-3' (SEQ ID NO: 39) and reverse primer 5'-TTTGGATCCGGGAAGGC-CTGGGCTGAAGCTACA-3' (SEQ ID NO: 40); and the the V-C-C region was amplified using forward primer 5'-TTTGCTAGCGCCACCATGGCAGCCGGAA-CAGCAGTT-3' (SEQ ID NO: 39) and reverse primer 5'-TTTGGATCCGTGGCTGGAATGGGTGGCCACACA-3' (SEQ ID NO: 41). The PCR products were digested using NheI and BamH1. Because of an internal BamHI site in the V-like domain of RAGE, the PCR products were cleaved into two fragments using NheI/BamHI: one with nucleotides 1-275 of SEQ ID NO: 2, the other with nucleotides 276-645 (V-C product) or 276-924 (V-C-C product). Cloning of sRAGE mimetibody into the IgG4 expression vectors involved two steps. First, the 1-275 fragment was cloned into the NheI/BamHI site of human IgG4 ΔCH1, Ser to Pro, Ala/Ala expression vector to generate an intermediate plasmid. The 276-645 or the 276-924 fragment was subsequently cloned into the BamHI site of the intermediate plasmid to generate plasmid expressing V-C or V-C-C sRAGE mimetibody, respectively.

To clone the V-only region into the IgG4 Ser to Pro, Ala/Ala scaffold, PCR was performed using forward primer 5'-TTTGCTAGCGCCACCATGGCAGCCGGAA-CAGCAGTT-3' (SEQ ID NO: 39) and reverse primer 5'-TTTGGATCCTCCATTCCTGTTCATTGC-CTGGCACCGGAAAATCCCCTCATCCT-GAATCCCGACAGCCG GAAGGAA-3' (SEQ ID NO: 42). The NheI/BamHI digested PCR product was cloned into the NheI/BamHI site of human IgG4 ΔCH1, Ser to Pro, Ala/Ala expression vector in a single step.

The IgG4 mimetibodies were transiently expressed in HEK293E cells and purified from the conditioned media using protein A affinity chromatography according to standard procedures.

Example 2

Binding of AGEs to sRAGE Mimetibody

To prepare AGE, bovine serum albumin (BSA, Fraction V) (Sigma, St. Louis, Mo.) was incubated under non-reducing conditions with 50 mM glycoaldehyde in phosphate buffered saline (PBS) (pH 7.4) without calcium chloride or magnesium chloride for 3 days at 37° C. To terminate the reaction, the AGE were dialyzed with 10 volumes of PBS (pH 7.4). The final protein concentration was determined using the Bicinchoninic Acid based protein assay (Pierce, Rockford, Ill.). Samples were determined to contain less than 1 endotoxin unit (EU) per microgram of protein using Limulus amebocyte lysate (LAL) testing.

Solid phase ELISA was used to assess mimetibody binding to AGE. Briefly, 96-well plates were coated overnight with 30 ug/ml AGE in 0.1 M Carbonate buffer, pH9.5 at 37° C. After washing in 0.15 M saline buffer containing 0.02% (w/v) Tween-20, the wells were blocked with 1%(w/v) BSA, 0.05% Tween-20 in PBS for 2 hours at 37° C. After washing, plates were incubated with varying concentrations of sRAGE mimetibody diluted in PBS for 45 minutes at 37° C. Plates were washed and probed with HRP-labeled goat anti-human Fc (Jackson ImmunoResearch, West Groove, Pa.) diluted 1:1000 in 1% BSA/PBS for 20 minutes at 37° C. Following another washing step, plates were incubated for 15 minutes at room temperature with 100 μL/well of Sigma 104 Phosphate Substrate (Sigma). Substrate development was stopped by addition of 25 μL/well sulfuric acid (4N) and the absorbance was measured at 490 nm via an automated plate spectrophotometer. As shown in FIG. 1, the mimetibodies tested all demonstrated binding to AGE. The binding affinities (KD) are shown in Table 2.

TABLE 2

Binding affinities (KD) of exemplary mimetibody constructs

| SEQ ID NO: | SRAGE domains | Ig isotype | KD (µg/ml) |
|---|---|---|---|
| 3 | V-C-C | IgG1, C220A, L234A/L235A | 0.62 |
| 5 | V | IgG1, C220A, L234A/L235A | 17.7 |
| 9 | V-C-C | IgG4, S228P, P234A/L235A | 0.18 |
| 11 | V-C | IgG4, S228P, P234A/L235A | 0.70 |
| 13 | V | IgG4, Ser−>Pro, Ala/Ala | 0.89 |

Example 3 sRAGE Mimetibody Reduces the Binding of AGE to RAGE

To measure the binding of the AGE to RAGE, a $^{125}$-I binding assay was performed. Cells that express RAGE (U937 cells) were cultured in DMEM media with 10% FBS and 1% L-Glutamine, Na Pyruvate and non-essential amino acids at 37° C., 5% $CO_2$, until $1.5 \times 10^6$ confluence was reached. Cells were plated in 96-well filter plates at 150,000 cells/well and incubated with 30 ug/ml Fc control (IgG4 mimetibody backbone without sRAGE encoding sequence) for 30 minutes at 37° C. to block Fc receptors. AGE were labeled with $^{125}$-I and the $^{125}$-I-AGEs were added to cells in two fold dilutions from 200 ug/ml to 0.1 ug/ml. After incubating at room temperature for 2 hours to allow maximal binding, the plates were filtered and washed with PBS to retain cells on the nitrocellulose membrane while allow unbound protein to pass through. The radioactivity on the membrane was measured using a Gamma counter. Non-specific binding was measured by co-incubation with 100+-fold excess of unlabeled AGE. The counts obtained from the non-specific binding were subtracted from the total binding data to determine specific binding. The affinity (KD) of AGE binding to U937 cells was calculated to be 11 ug/ml.

Figure 2:
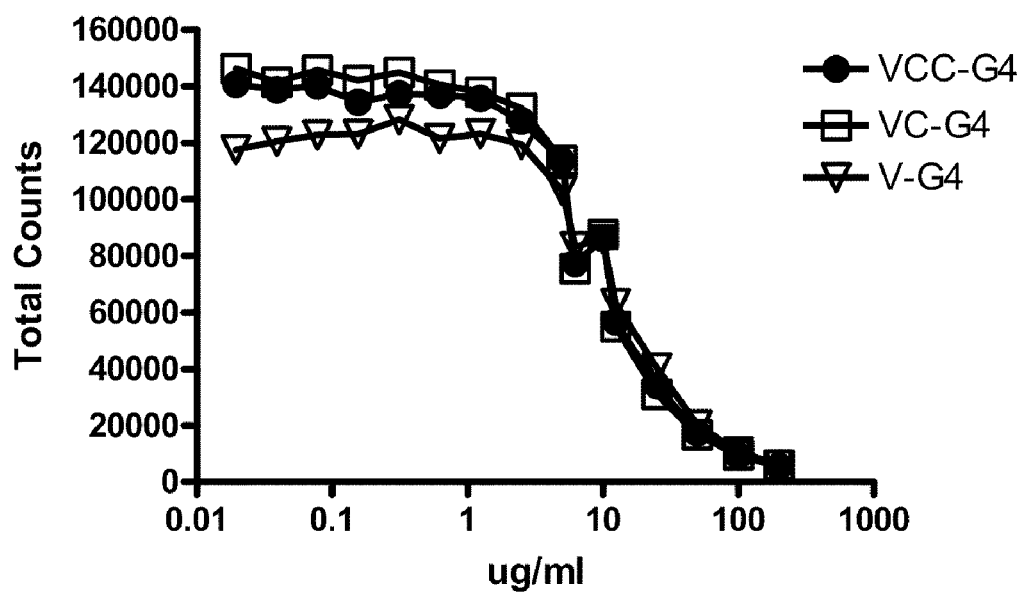
FIG. 2 shows the reduction of AGE binding to U937 cells by sRAGE mimetibodies.
Figure 3A:
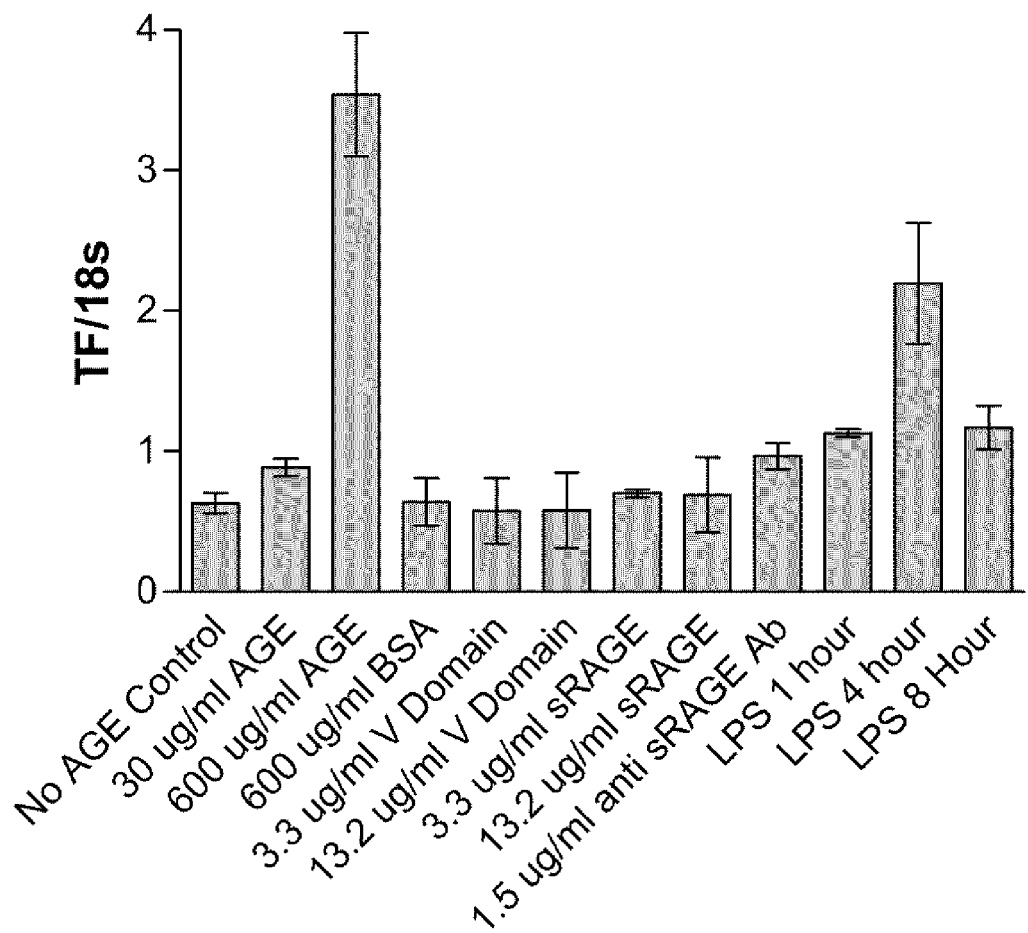
FIGS. 3A to 3E show sRAGE mimetibody inhibition of AGE-induced mRNA expression for tissue factor (FIG. 3A); VEGF (FIG. 3B); E-selectin (FIG. 3C); RAGE (FIG. 3D); and IL-6 (FIG. 3E).
Figure 3B:
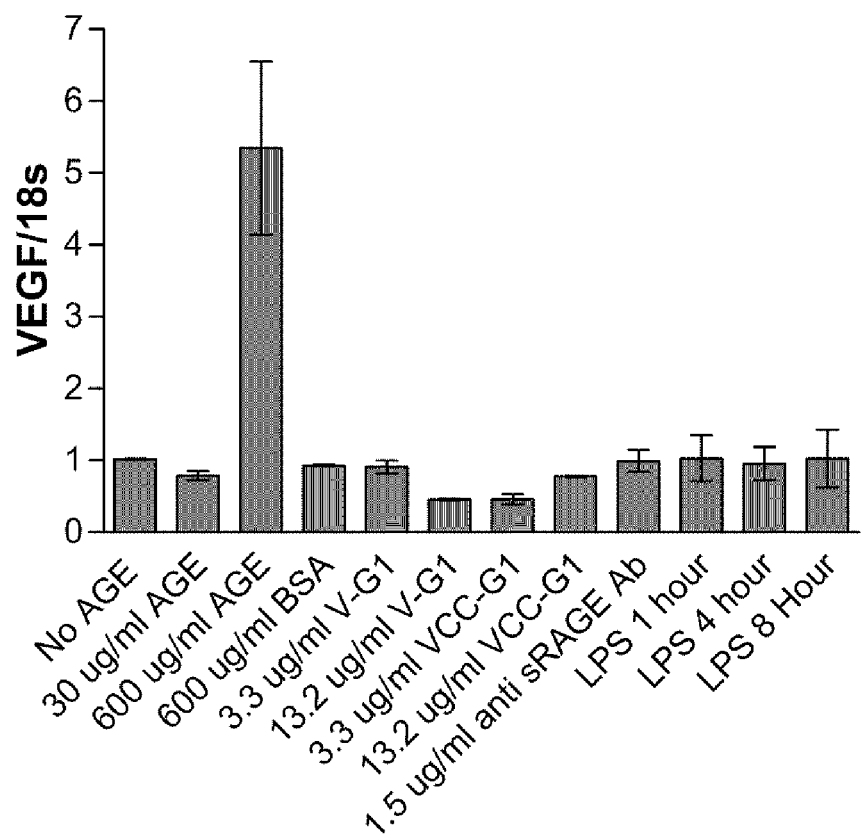
Figure 3C:
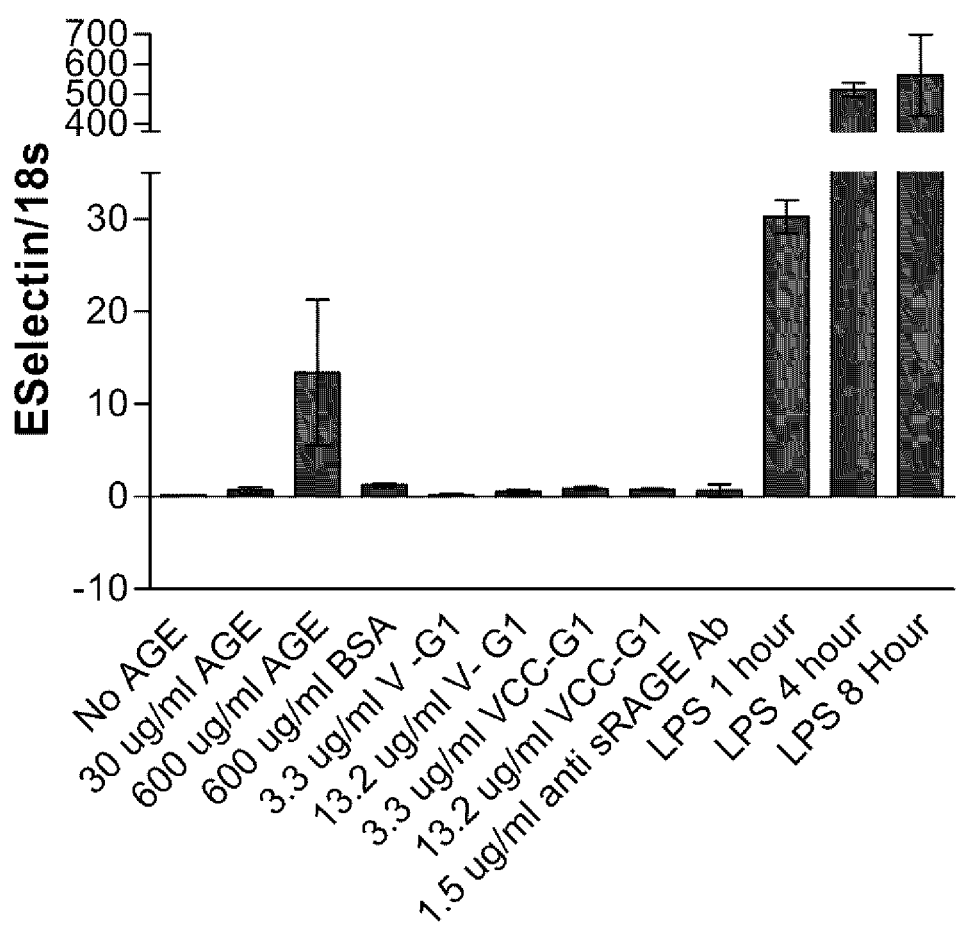
Figure 3D:
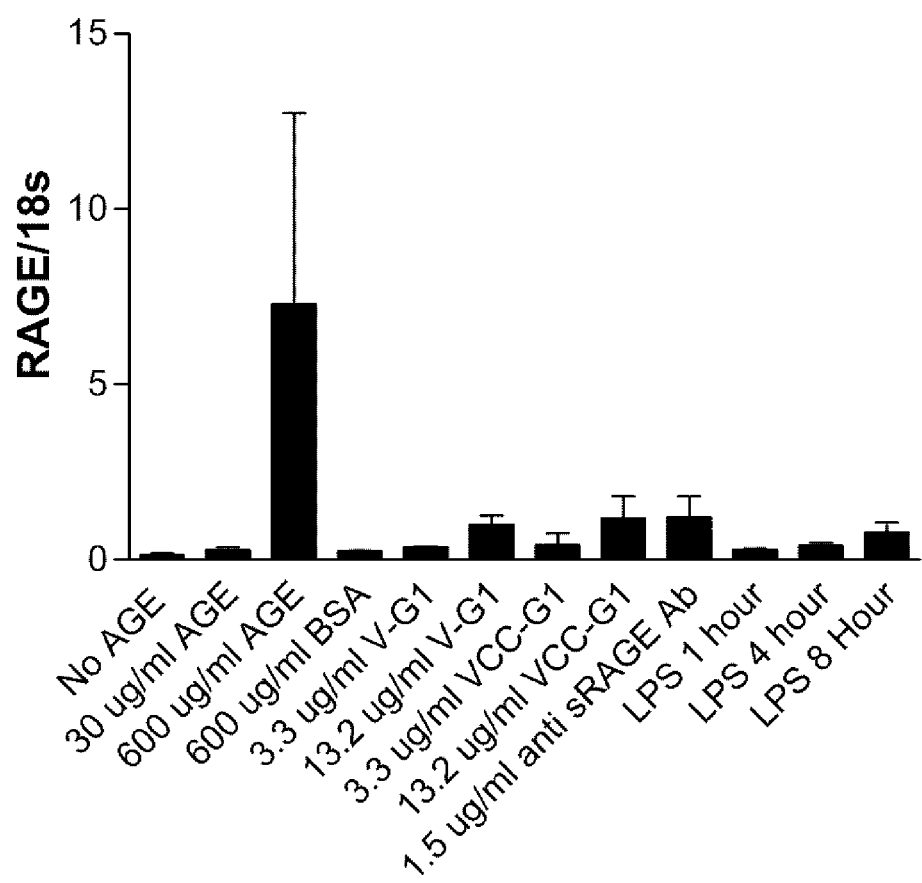
Figure 3E:
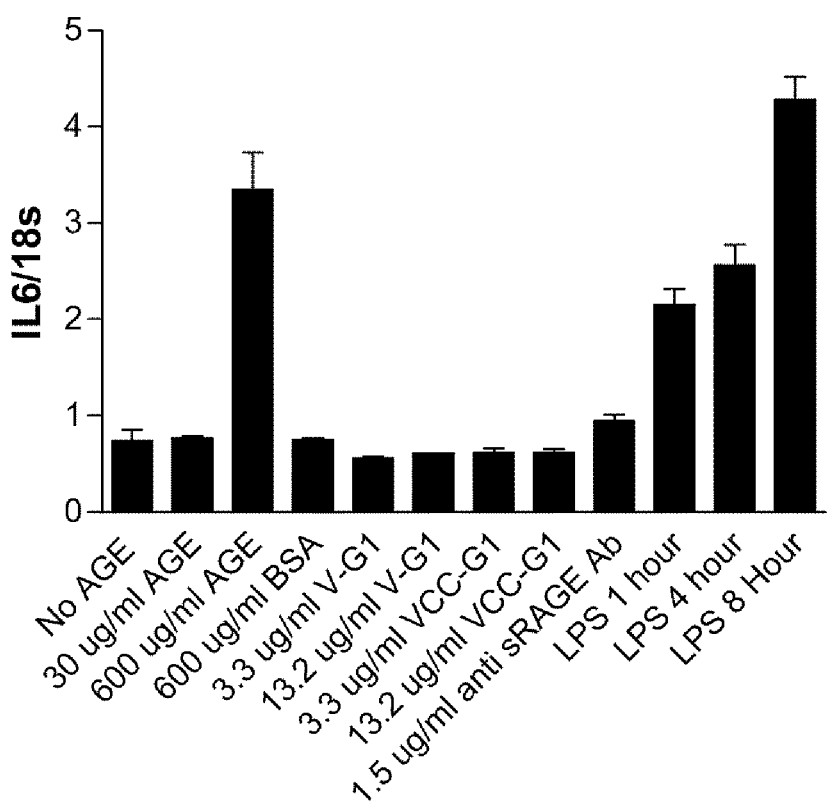

The ability of the sRAGE MMBs to reduce AGE binding to U937 cells was determined by a competition assay. Briefly, $^{125}$-I-AGE (11 ug/ml) were incubated with sRAGE mimetibodies for 2 hours. The mimetibodies used were diluted two fold from 200 ug/ml to 0.1 ug/ml. The mixture of $^{125}$-I-AGE and sRAGE mimetibodies was added to U937 and the binding of AGEs to U937 was measured using the binding assay described above. As shown in FIG. 2, sRAGE mimetibodies tested demonstrated reduction of AGE binding to the U937 cells. IC50 of the tested mimetibodies were calculated at approximately 90 nM.

Example 4 sRAGE Mimetibody Reduces AGE-Induced Gene Expression

To show AGE stimulation of expression of certain genes, human umbilical endothelial cells (HUVEC) were incubated with 30 ug/ml AGE, 600 ug/ml AGE, for 1, 4, 8 or 12 hours. As a positive control, cells were incubated with 13 ug/ml Lipopolysaccharide (LPS), an inflammatory stimulant. As a negative control, cells were incubated with 600 ug/ml BSA. Cells were harvested and total RNA was isolated using RNeasy (Qiagen, Valencia, Calif.). The RNA was quantitated with the Agilent Bioanalyzer. Quantitative PCR was performed using Assay-on-Demand primers (Applied Biosystems, Foster City, Calif.) for E-Selectin (HS00174057), RAGE (HS00153957), VEGF (HS00173626), IL-6 (HS00174131), GAPDH (HS99999905) and Tissue Factor (HS00175225). The RT-PCR products were quantitated relative to 18s RNA. As shown in FIG. 3, AGE, but not control BSA, increased the mRNA level of each of the genes tested.

To demonstrate the ability of sRAGE mimetibodies to inhibit AGE-stimulated mRNA levels, HUVEC cells were incubated with 3.3 ug/ml sRAGE mimetibody in addition to 600 ug/ml AGE or 13.2 ug/ml sRAGE mimetibody in addition to 600 ug/ml AGE. RNA purification and quantitative PCR were performed as described above. As shown in FIG. 3, sRAGE mimetibodies inhibited the AGE-induction of the transcripts encoding (3A) Tissue Factor, (3B) VEGF, (3C) E-Selectin, (3D) RAGE, and (3E) IL-6.

The present invention now being fully described, it will be apparent to one of ordinary skill in the art that many changes and modifications can be made thereto without departing from the spirit or scope of the appended claims.

The invention claimed is:

1. A polypeptide according to formula (I):

$$(Rg\text{-}Lk\text{-}V2\text{-}Hg\text{-}C_H2\text{-}C_H3)_{(t)} \quad (I)$$

where Rg is a mammalian sRAGE sequence, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10, wherein Cys220 of Hg is substituted with Ala, and Leu234 and Leu235 of $C_H2$-$C_H3$ are mutated to Ala234 and Ala235.

2. The polypeptide of claim 1 wherein Hg, $C_H2$ and $C_H3$ are of the IgG1 subclass.

3. The polypeptide of claim 1 wherein Hg is of the IgG4 subclass, and $C_H2$ and $C_H3$ are of the IgG1 subclass.

4. The polypeptide of claim 1 wherein Ser228 of Hg is substituted with Pro.

5. A pharmaceutical composition comprising an effective amount of at least one polypeptide according to claim 1 and a pharmaceutically acceptable carrier or diluent.

* * * * *

SEQUENCE LISTING

```
<160> NUMBER OF SEQ ID NOS: 42

<210> SEQ ID NO 1
<211> LENGTH: 308
<212> TYPE: PRT
<213> ORGANISM: Homo sapiens

<400> SEQUENCE: 1

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80
```

```
Asn Gly Ser Leu Phe Leu Pro Ala Val Gly Ile Gln Asp Glu Gly Ile
                85                  90                  95
Phe Arg Cys Gln Ala Met Asn Arg Asn Gly Lys Glu Thr Lys Ser Asn
            100                 105                 110
Tyr Arg Val Arg Val Tyr Gln Ile Pro Gly Lys Pro Glu Ile Val Asp
        115                 120                 125
Ser Ala Ser Glu Leu Thr Ala Gly Val Pro Asn Lys Val Gly Thr Cys
    130                 135                 140
Val Ser Glu Gly Ser Tyr Pro Ala Gly Thr Leu Ser Trp His Leu Asp
145                 150                 155                 160
Gly Lys Pro Leu Val Pro Asn Glu Lys Gly Val Ser Val Lys Glu Gln
                165                 170                 175
Thr Arg Arg His Pro Glu Thr Gly Leu Phe Thr Leu Gln Ser Glu Leu
            180                 185                 190
Met Val Thr Pro Ala Arg Gly Gly Asp Pro Arg Pro Thr Phe Ser Cys
        195                 200                 205
Ser Phe Ser Pro Gly Leu Pro Arg His Arg Ala Leu Arg Thr Ala Pro
    210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
        275                 280                 285
Pro Glu Ile Gly Pro Gln Asp Gln Gly Thr Tyr Ser Cys Val Ala Thr
    290                 295                 300
His Ser Ser His
305

<210> SEQ ID NO 2
<211> LENGTH: 924
<212> TYPE: DNA
<213> ORGANISM: Homo sapiens

<400> SEQUENCE: 2
atggcagccg gaacagcagt tggagcctgg gtgctggtcc tcagtctgtg gggggcagta    60
gtaggtgctc aaaacatcac agcccggatt ggcgagccac tggtgctgaa gtgtaagggg    120
gcccccaaga aaccaccccca gcggctggaa tggaaactga acacaggccg gacagaagct    180
tggaaggtcc tgtctcccca gggaggaggc ccctgggaca gtgtggctcg tgtccttccc    240
aacggctccc tcttccttcc ggctgtcggg atccaggatg aggggatttt ccggtgccag    300
gcaatgaaca ggaatggaaa ggagaccaag tccaactacc gagtccgtgt ctaccagatt    360
cctgggaagc cagaaattgt agattctgcc tctgaactca cggctggtgt tccaataag     420
gtggggacat gtgtgtcaga gggaagctac cctgcaggga ctcttagctg gcacttggat    480
gggaagcccc tggtgcctaa tgagaaggga gtatctgtga aggaacagac caggagacac    540
cctgagacag gctcttcac actgcagtcg gagctaatgg tgaccccagc cggggagga     600
gatcccgtc ccaccttctc ctgtagcttc agcccaggcc ttccccgaca ccgggccttg    660
cgcacagccc ccatccagcc ccgtgtctgg gagcctgtgc ctctggagga ggtccaattg    720
gtggtggagc cagaaggtgg agcagtagct cctggtggaa ccgtaaccct gacctgtgaa    780
```

-continued

```
gtccctgccc agccctctcc tcaaatccac tggatgaagg atggtgtgcc cttgccccctt   840 ccccccagcc ctgtgctgat cctccctgag atagggcctc aggaccaggg aacctacagc    900
tgtgtggcca cccattccag ccac                                           924
```

<210> SEQ ID NO 3
<211> LENGTH: 548
<212> TYPE: PRT
<213> ORGANISM: Artificial Sequence
<220> FEATURE:
<223> OTHER INFORMATION: sRAGE Mimetibody binding to AGEs

<400> SEQUENCE: 3

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Thr Leu Val Thr Val Ser Ser Glu Pro Lys Ser
305                 310                 315                 320

Ala Asp Lys Thr His Thr Cys Pro Pro Cys Pro Ala Pro Glu Ala Ala
                325                 330                 335

Gly Gly Pro Ser Val Phe Leu Phe Pro Pro Lys Pro Lys Asp Thr Leu
```

```
                    340            345             350
Met Ile Ser Arg Thr Pro Glu Val Thr Cys Val Val Asp Val Ser
                355                 360                 365

His Glu Asp Pro Glu Val Lys Phe Asn Trp Tyr Val Asp Gly Val Glu
    370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Pro
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Arg Asp Glu Leu Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
        515                 520                 525

Met His Glu Ala Leu His Asn His Tyr Thr Gln Lys Ser Leu Ser Leu
    530                 535                 540

Ser Pro Gly Lys
545

<210> SEQ ID NO 4
<211> LENGTH: 1647
<212> TYPE: DNA
<213> ORGANISM: Artificial Sequence
<220> FEATURE:
<223> OTHER INFORMATION: sRAGE Mimetibody binding to AGEs.

<400> SEQUENCE: 4
atggcagccg aacagcagt tgagcctgg gtgctggtcc tcagtctgtg gggggcagta      60
gtaggtgctc aaaacatcac agcccggatt ggcgagccac tggtgctgaa gtgtaagggg    120
gcccccaaga accacccca gcggctgaa tggaaactga acacaggccg acagaagct       180 tggaaggtcc tgtctcccca gggaggaggc ccctgggaca gtgtggctcg tgtccttccc    240
aacggctccc tcttccttcc ggctgtcggg atccaggatg aggggatttt ccggtgccag    300
gcaatgaaca ggaatggaaa ggagaccaag tccaactacc gagtccgtgt ctaccagatt    360
cctgggaagc agaaattgt agattctgcc tctgaactca cggctggtgt tcccaataag    420
gtggggacat gtgtgtcaga gggaagctac cctgcaggga ctcttagctg gcacttggat    480
gggaagcccc tggtgcctaa tgagaaggga gtatctgtga ggaacagac caggagacac    540 cctgagacag ggctcttcac actgcagtcg gagctaatgg tgaccccagc ccggggagga    600
gatccccgtc ccaccttctc ctgtagcttc agcccaggcc ttccccgaca ccgggccttg    660
cgcacagccc ccatccagcc ccgtgtctgg agcctgtgc tctggagga ggtccaattg     720 gtggtggagc cagaaggtgg agcagtagct cctggtggaa ccgtaaccct gacctgtgaa    780
gtccctgccc agccctctcc tcaaatccac tggatgaagg atggtgtgcc cttgcccctt    840
ccccccagcc ctgtgctgat cctccctgag atagggcctc aggaccaggg aacctacagc    900
```

```
tgtgtggcca cccattccag ccacggtacc ttagtcaccg tctcctcaga gcccaaatct   960
gctgacaaaa ctcacacatg cccaccgtgc ccagcacctg aagccgccgg gggaccgtca  1020
gtcttcctct ccccccaaa acccaaggac accctcatga tctcccggac ccctgaggtc  1080
acatgcgtgg tggtggacgt gagccacgaa gaccctgagg tcaagttcaa ctggtacgtg  1140
gacggcgtgg aggtgcataa tgccaagaca aagccgcggg aggagcagta caacagcacg  1200
taccgggtgg tcagcgtcct caccgtcctg caccaggact ggctgaatgg caaggagtac  1260
aagtgcaagg tctccaacaa agccctccca gcccccatcg agaaaaccat ctccaaagcc  1320
aaagggcagc cccgagaacc acaggtgtac accctgcccc catcccggga tgagctgacc  1380
aagaaccagg tcagcctgac ctgcctggtc aaaggcttct atcccagcga catcgccgtg  1440
gagtgggaga gcaatgggca gccggagaac aactacaaga ccacgcctcc cgtgctggac  1500
tccgacggct ccttcttcct ctacagcaag ctcaccgtgg acaagagcag gtggcagcag  1560
gggaacgtct tctcatgctc cgtgatgcat gaggctctgc acaaccacta cacgcagaag  1620
agcctctccc tgtctccggg taaatga                                      1647
```

<210> SEQ ID NO 5
<211> LENGTH: 346
<212> TYPE: PRT
<213> ORGANISM: Artificial Sequence
<220> FEATURE:
<223> OTHER INFORMATION: sRAGE Mimetibody binding to AGEs.

<400> SEQUENCE: 5

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Gly Thr Leu Val Thr Val
            100                 105                 110

Ser Ser Glu Pro Lys Ser Ala Asp Lys Thr His Thr Cys Pro Pro Cys
        115                 120                 125

Pro Ala Pro Glu Ala Ala Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
```

```
             225                 230                 235                 240
Gln Pro Arg Glu Pro Gln Val Tyr Thr Leu Pro Pro Ser Arg Asp Glu
            245                 250                 255

Leu Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly Lys
            340                 345

<210> SEQ ID NO 6
<211> LENGTH: 1041
<212> TYPE: DNA
<213> ORGANISM: Artificial Sequence
<220> FEATURE:
<223> OTHER INFORMATION: sRAGE Mimetibody binding to AGEs.

<400> SEQUENCE: 6
atggcagccg gaacagcagt tggagcctgg gtgctggtcc tcagtctgtg gggggcagta        60
gtaggtgctc aaaacatcac agcccggatt ggcgagccac tggtgctgaa gtgtaagggg       120
gcccccaaga accaccccca gcggctggaa tggaaactga acacaggccg gacagaagct       180
tggaaggtcc tgtctcccca gggaggaggc ccctgggaca gtgtggctcg tgtccttccc       240
aacggctccc tcttccttcc ggctgtcggg atccaggatg aggggatttt ccggtgccag       300
gcaatgaaca ggaatggagg taccttagtc accgtctcct cagagcccaa atctgctgac       360
aaaactcaca catgcccacc gtgcccagca cctgaagccg ccggggggacc gtcagtcttc       420
ctcttccccc caaaacccaa ggacacccct catgatctcc cggaccctga ggtcacatgc       480
gtggtggtgg acgtgagcca cgaagaccct gaggtcaagt tcaactggta cgtggacggc       540
gtggaggtgc ataatgccaa gacaaagccg cgggaggagc agtacaacag cacgtaccgg       600
gtggtcagcg tcctcaccgt cctgcaccag gactggctga atggcaagga gtacaagtgc       660
aaggtctcca acaaagccct cccagccccc atcgagaaaa ccatctccaa agccaaaggg       720
cagccccgag aaccacaggt gtacaccctg cccccatccc gggatgagct gaccaagaac       780
caggtcagcc tgacctgcct ggtcaaaggc ttctatccca gcgacatcgc cgtggagtgg       840
gagagcaatg ggcagccgga gaacaactac aagaccacgc ctcccgtgct ggactccgac       900
ggctccttct cctctacag caagctcacc gtggacaaga gcaggtggca gcagggaaac       960
gtcttctcat gctccgtgat gcatgaggct ctgcacaacc actacacgca gaagagcctc      1020
tccctgtctc cgggtaaatg a                                                1041

<210> SEQ ID NO 7
<211> LENGTH: 551
<212> TYPE: PRT
<213> ORGANISM: Artificial Sequence
<220> FEATURE:
<223> OTHER INFORMATION: sRAGE Mimetibody binding to AGEs.

<400> SEQUENCE: 7

Met Ala Ala Gly Thr Ala Val Gly Ala Trp Val Leu Val Leu Ser Leu
```

-continued

```
 1               5                   10                  15
Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
            50                  55                  60

Ser Pro Gln Gly Gly Pro Trp Asp Ser Val Ala Arg Val Leu Pro
 65                  70                  75                  80

Asn Gly Ser Leu Phe Leu Pro Ala Val Gly Ile Gln Asp Glu Gly Ile
                    85                  90                  95

Phe Arg Cys Gln Ala Met Asn Arg Asn Gly Lys Glu Thr Lys Ser Asn
                    100                 105                 110

Tyr Arg Val Arg Val Tyr Gln Ile Pro Gly Lys Pro Glu Ile Val Asp
                    115                 120                 125

Ser Ala Ser Glu Leu Thr Ala Gly Val Pro Asn Lys Val Gly Thr Cys
                    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                    165                 170                 175

Thr Arg Arg His Pro Glu Thr Gly Leu Phe Thr Leu Gln Ser Glu Leu
                    180                 185                 190

Met Val Thr Pro Ala Arg Gly Gly Asp Pro Arg Pro Thr Phe Ser Cys
                    195                 200                 205

Ser Phe Ser Pro Gly Leu Pro Arg His Arg Ala Leu Arg Thr Ala Pro
                    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                    245                 250                 255

Leu Thr Cys Glu Val Pro Ala Gln Pro Ser Pro Gln Ile His Trp Met
                    260                 265                 270

Lys Asp Gly Val Pro Leu Pro Leu Pro Pro Ser Pro Val Leu Ile Leu
                    275                 280                 285

Pro Glu Ile Gly Pro Gln Asp Gln Gly Thr Tyr Ser Cys Val Ala Thr
                    290                 295                 300

His Ser Ser His Gly Ser Gly Gly Ser Gly Thr Leu Val Thr Val
305                 310                 315                 320

Ser Ser Glu Ser Lys Tyr Gly Pro Pro Cys Pro Ser Cys Pro Ala Pro
                    325                 330                 335

Glu Phe Leu Gly Gly Pro Ser Val Phe Leu Phe Pro Pro Lys Pro Lys
                    340                 345                 350

Asp Thr Leu Met Ile Ser Arg Thr Pro Glu Val Thr Cys Val Val Val
                    355                 360                 365

Asp Val Ser Gln Glu Asp Pro Glu Val Gln Phe Asn Trp Tyr Val Asp
                    370                 375                 380

Gly Val Glu Val His Asn Ala Lys Thr Lys Pro Arg Glu Glu Gln Phe
385                 390                 395                 400

Asn Ser Thr Tyr Arg Val Val Ser Val Leu Thr Val Leu His Gln Asp
                    405                 410                 415

Trp Leu Asn Gly Lys Glu Tyr Lys Cys Lys Val Ser Asn Lys Gly Leu
                    420                 425                 430
```

```
Pro Ser Ser Ile Glu Lys Thr Ile Ser Lys Ala Lys Gly Gln Pro Arg
        435                 440                 445
Glu Pro Gln Val Tyr Thr Leu Pro Pro Ser Gln Glu Met Thr Lys
    450                 455                 460
Asn Gln Val Ser Leu Thr Cys Leu Val Lys Gly Phe Tyr Pro Ser Asp
465                 470                 475                 480
Ile Ala Val Glu Trp Glu Ser Asn Gly Gln Pro Glu Asn Asn Tyr Lys
                485                 490                 495
Thr Thr Pro Pro Val Leu Asp Ser Asp Gly Ser Phe Phe Leu Tyr Ser
            500                 505                 510
Arg Leu Thr Val Asp Lys Ser Arg Trp Gln Gln Gly Asn Val Phe Ser
        515                 520                 525
Cys Ser Val Met His Glu Ala Leu His Asn His Tyr Thr Gln Lys Ser
530                 535                 540
Leu Ser Leu Ser Leu Gly Lys
545             550

<210> SEQ ID NO 8
<211> LENGTH: 1656
<212> TYPE: DNA
<213> ORGANISM: Artificial Sequence
<220> FEATURE:
<223> OTHER INFORMATION: sRAGE Mimetibody binding to AGEs.

<400> SEQUENCE: 8
atggcagccg aacagcagt tggagcctgg gtgctggtcc tcagtctgtg ggggcagta       60
gtaggtgctc aaaacatcac agcccggatt ggcgagccac tggtgctgaa gtgtaagggg     120
gcccccaaga accacccca gcggctggaa tggaaactga cacaggccg acagaagct       180
tggaaggtcc tgtctcccca gggaggaggc ccctgggaca gtgtggctcg tgtccttccc     240
aacggctccc tcttccttcc ggctgtcgg atccaggatg aggggatttt ccggtgccag      300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga gggaagctac ctgcagggac tcttagctg gcacttggat      480
gggaagcccc tggtgcctaa tgagaaggga gtatctgtga aggaacagac caggagacac     540
cctgagacag ggctcttcac actgcagtcg gagctaatgg tgaccccagc ccggggagga    600
gatccccgtc ccaccttctc ctgtagcttc agcccaggcc ttccccgaca ccgggccttg     660
cgcacagccc ccatccagcc ccgtgtctgg agcctgtgc ctctggagga ggtccaattg      720
gtggtggagc cagaaggtgg agcagtagct cctggtggaa ccgtaaccct gacctgtgaa    780
gtccctgccc agccctctcc tcaaatccac tggatgaagg atggtgtgcc cttgccctt     840
cccccccagcc ctgtgctgat cctccctgag atagggcctc aggaccaggg aacctacagc    900
tgtgtggcca cccattccag ccacggatcc ggtgaggct ccgtaccctt agtcaccgtc      960
tcctcagagt ccaaatatgg tccccatgc catcatgcc cggcgcctga gttcctgggg       1020
ggaccatcag tcttcctgtt ccccccaaaa cccaaggaca ctctcatgat ctcccggacc    1080
cctgaggtca cgtgcgtggt ggtggacgtg agccaggaag accccgaggt ccagttcaac    1140
tggtacgtgg atggcgtgga ggtgcataat gccaagacaa agccgcggga ggagcagttc    1200
aacagcacgt accgtgtggt cagcgtcctc accgtcctgc accaggactg gctgaacggc    1260
aaggagtaca agtgcaaggt ctccaacaaa ggcctcccgt cctccatcga gaaaaccatc   1320
tccaaagcca aagggcagcc tcgagagcca caggtgtaca ccctgccccc atcccaggag    1380
```

-continued

```
gagatgacca agaaccaggt cagcctgacc tgcctggtca aaggcttcta ccccagcgac   1440
atcgccgtgg agtgggagag caatgggcag ccggagaaca actacaagac cacgcctccc   1500
gtgctggact ccgacggctc cttcttcctc tacagcaggc taaccgtgga caagagcagg   1560
tggcaggagg ggaatgtctt ctcatgctcc gtgatgcatg aggctctgca caaccactac   1620
acacagaaaa gcttgtccct gtctctgggt aaatga                             1656
```

<210> SEQ ID NO 9
<211> LENGTH: 551
<212> TYPE: PRT
<213> ORGANISM: Artificial Sequence
<220> FEATURE:
<223> OTHER INFORMATION: sRAGE Mimetibody binding to AGEs.

<400> SEQUENCE: 9

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Ser Gly Gly Ser Gly Thr Leu Val Thr Val
305                 310                 315                 320
```

```
Ser Ser Glu Ser Lys Tyr Gly Pro Pro Cys Pro Cys Pro Ala Pro
            325                 330                 335

Glu Ala Ala Gly Gly Pro Ser Val Phe Leu Phe Pro Pro Lys Pro Lys
            340                 345                 350

Asp Thr Leu Met Ile Ser Arg Thr Pro Glu Val Thr Cys Val Val Val
            355                 360                 365

Asp Val Ser Gln Glu Asp Pro Glu Val Gln Phe Asn Trp Tyr Val Asp
            370                 375                 380

Gly Val Glu Val His Asn Ala Lys Thr Lys Pro Arg Glu Glu Gln Phe
385                 390                 395                 400

Asn Ser Thr Tyr Arg Val Val Ser Val Leu Thr Val Leu His Gln Asp
            405                 410                 415

Trp Leu Asn Gly Lys Glu Tyr Lys Cys Lys Val Ser Asn Lys Gly Leu
            420                 425                 430

Pro Ser Ser Ile Glu Lys Thr Ile Ser Lys Ala Lys Gly Gln Pro Arg
            435                 440                 445

Glu Pro Gln Val Tyr Thr Leu Pro Pro Ser Gln Glu Glu Met Thr Lys
            450                 455                 460

Asn Gln Val Ser Leu Thr Cys Leu Val Lys Gly Phe Tyr Pro Ser Asp
465                 470                 475                 480

Ile Ala Val Glu Trp Glu Ser Asn Gly Gln Pro Glu Asn Asn Tyr Lys
            485                 490                 495

Thr Thr Pro Pro Val Leu Asp Ser Asp Gly Ser Phe Phe Leu Tyr Ser
            500                 505                 510

Arg Leu Thr Val Asp Lys Ser Arg Trp Gln Gln Gly Asn Val Phe Ser
            515                 520                 525

Cys Ser Val Met His Glu Ala Leu His Asn His Tyr Thr Gln Lys Ser
            530                 535                 540

Leu Ser Leu Ser Leu Gly Lys
545                 550

<210> SEQ ID NO 10
<211> LENGTH: 1656
<212> TYPE: DNA
<213> ORGANISM: Artificial Sequence
<220> FEATURE:
<223> OTHER INFORMATION: sRAGE Mimetibody binding to AGEs.

<400> SEQUENCE: 10
atggcagccg aacagcagt tggagcctgg tgctggtcc tcagtctgtg gggggcagta      60
gtaggtgctc aaaacatcac agcccggatt ggcgagccac tggtgctgaa gtgtaagggg    120
gcccccaaga accacccca gcggctggaa tggaaactga acacaggccg acagaagct     180 tggaaggtcc tgtctcccca gggaggaggc ccctgggaca gtgtggctcg tgtccttccc   240
aacggctccc tcttccttcc ggctgtcggg atccaggatg agggattttt ccggtgccag   300
gcaatgaaca ggaatggaaa ggagaccaag tccaactacc gagtccgtgt ctaccagatt   360
cctgggaagc cagaaattgt agattctgcc tctgaactca cggctggtgt tcccaataag   420
gtggggacat gtgtgtcaga gggaagctac cctgcaggga ctcttagctg gcacttggat   480
gggaagcccc tggtgcctaa tgagaaggga gtatctgtga aggaacagac caggagacac   540
cctgagacag ggctcttcac actgcagtcg gagctaatgg tgaccccagc ccggggagga   600
gatccccgtc ccaccttctc ctgtagcttc agcccaggcc ttccccgaca ccgggccttg   660
cgcacagccc ccatccagcc ccgtgtctgg gagcctgtgc ctctggagga ggtccaattg   720
gtggtggagc cagaaggtgg agcagtagct cctggtggaa ccgtaaccct gacctgtgaa    780
```

```
gtccctgccc agccctctcc tcaaatccac tggatgaagg atggtgtgcc cttgccccttt      840 ccccccagcc ctgtgctgat cctccctgag atagggcctc aggaccaggg aacctacagc      900
tgtgtggcca cccattccag ccacggatcc ggtggaggct ccggtacctt agtcaccgtc      960
tcctcagagt ccaaatatgg tccccatgc ccaccatgcc cggcgcctga ggccgccggg     1020
ggaccatcag tcttcctgtt ccccccaaaa cccaaggaca ctctcatgat ctcccggacc     1080
cctgaggtca cgtgcgtggt ggtggacgtg agccaggaag accccgaggt ccagttcaac     1140
tggtacgtgg atggcgtgga ggtgcataat gccaagacaa agccgcggga ggagcagttc     1200
aacagcacgt accgtgtggt cagcgtcctc accgtcctgc accaggactg gctgaacggc     1260
aaggagtaca agtgcaaggt ctccaacaaa ggcctcccgt cctccatcga aaaaccatc      1320 tccaaagcca aagggcagcc tcgagagcca caggtgtaca ccctgccccc atcccaggag     1380
gagatgacca gaaccaggt cagcctgacc tgcctggtca aaggcttcta ccccagcgac      1440
atcgccgtgg agtgggagag caatgggcag ccggagaaca actacaagac cacgcctccc     1500
gtgctggact ccgacggctc cttcttcctc tacagcaggc taaccgtgga caagagcagg     1560
tggcaggagg ggaatgtctt ctcatgctcc gtgatgcatg aggctctgca caaccactac     1620
acacagaaaa gcttgtccct gtctctgggt aaatga                              1656
```

<210> SEQ ID NO 11
<211> LENGTH: 458
<212> TYPE: PRT
<213> ORGANISM: Artificial Sequence
<220> FEATURE:
<223> OTHER INFORMATION: sRAGE Mimetibody binding to AGEs.

<400> SEQUENCE: 11

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205
```

```
Ser Phe Ser Pro Gly Leu Pro Gly Ser Gly Gly Ser Gly Thr Leu
    210                 215                 220
Val Thr Val Ser Ser Glu Ser Lys Tyr Gly Pro Cys Pro Pro Cys
225                 230                 235                 240
Pro Ala Pro Glu Ala Ala Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser Gln Glu Asp Pro Glu Val Gln Phe Asn Trp
        275                 280                 285
Tyr Val Asp Gly Val Glu Val His Asn Ala Lys Thr Lys Pro Arg Glu
    290                 295                 300
Glu Gln Phe Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Gly Leu Pro Ser Ser Ile Glu Lys Thr Ile Ser Lys Ala Lys Gly
            340                 345                 350
Gln Pro Arg Glu Pro Gln Val Tyr Thr Leu Pro Pro Ser Gln Glu Glu
        355                 360                 365
Met Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Arg Leu Thr Val Asp Lys Ser Arg Trp Gln Glu Gly Asn
            420                 425                 430
Val Phe Ser Cys Ser Val Met His Glu Ala Leu His Asn His Tyr Thr
        435                 440                 445
Gln Lys Ser Leu Ser Leu Ser Leu Gly Lys
    450                 455

<210> SEQ ID NO 12
<211> LENGTH: 1377
<212> TYPE: DNA
<213> ORGANISM: Artificial Sequence
<220> FEATURE:
<223> OTHER INFORMATION: mimetibody cDNA

<400> SEQUENCE: 12
atggcagccg aacagcagt tggagcctgg gtgctggtcc tcagtctgtg gggggcagta      60
gtaggtgctc aaaacatcac agcccggatt ggcgagccac tggtgctgaa gtgtaagggg     120
gcccccaaga aaccaccca gcggctggaa tggaaactga acacaggccg acagaagct      180
tggaaggtcc tgtctcccca gggaggaggc ccctgggaca gtgtggctcg tgtccttccc     240
aacggctccc tcttccttcc ggctgtcggg atccaggatg aggggatttt ccggtgccag     300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga gggaagctac cctgcaggga ctcttagctg cacttggat     480
gggaagcccc tggtgcctaa tgagaaggga gtatctgtga aggaacagac caggagacac     540
ctgagacag ggctcttcac actgcagtcg gagctaatgg tgaccccagc ccggggagga     600
gatcccgtc ccaccttctc ctgtagcctt agcccaggcc ttcccggatc cggtggaggc     660
```

-continued

```
tccggtacct tagtcaccgt ctcctcagag tccaaatatg gtcccccatg cccaccatgc    720
ccggcgcctg aggccgccgg gggaccatca gtcttcctgt tccccccaaa acccaaggac    780
actctcatga tctcccggac ccctgaggtc acgtgcgtgg tggtggacgt gagccaggaa    840
gaccccgagg tccagttcaa ctggtacgtg gatggcgtgg aggtgcataa tgccaagaca    900
aagccgcggg aggagcagtt caacagcacg taccgtgtgg tcagcgtcct caccgtcctg    960
caccaggact ggctgaacgg caaggagtac aagtgcaagg tctccaacaa aggcctcccg   1020
tcctccatcg agaaaaccat ctccaaagcc aagggcagc ctcgagagcc acaggtgtac    1080
accctgcccc catcccagga ggagatgacc aagaaccagg tcagcctgac ctgcctggtc    1140
aaaggcttct accccagcga catcgccgtg gagtgggaga gcaatgggca gccggagaac   1200
aactacaaga ccacgcctcc cgtgctggac tccgacggct ccttcttcct ctacagcagg   1260
ctaaccgtgg acaagagcag gtggcaggag gggaatgtct tctcatgctc cgtgatgcat   1320
gaggctctgc acaaccacta cacacagaaa agcttgtccc tgtctctggg taaatga      1377
```

<210> SEQ ID NO 13
<211> LENGTH: 349
<212> TYPE: PRT
<213> ORGANISM: Artificial Sequence
<220> FEATURE:
<223> OTHER INFORMATION: sRAGE Mimetibody binding to AGEs.

<400> SEQUENCE: 13

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Gly Ser Gly Gly Gly Ser
            100                 105                 110

Gly Thr Leu Val Thr Val Ser Ser Glu Ser Lys Tyr Gly Pro Pro Cys
        115                 120                 125

Pro Pro Cys Pro Ala Pro Glu Ala Ala Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
```

```
                    245                 250                 255
Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
            275                 280                 285

Pro Glu Asn Asn Tyr Lys Thr Thr Pro Pro Val Leu Asp Ser Asp Gly
            290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 14
<211> LENGTH: 1050
<212> TYPE: DNA
<213> ORGANISM: Artificial Sequence
<220> FEATURE:
<223> OTHER INFORMATION: sRAGE Mimetibody binding to AGEs.

<400> SEQUENCE: 14

```
atggcagccg aacagcagt tggagcctgg gtgctggtcc tcagtctgtg gggggcagta      60
gtaggtgctc aaaacatcac agcccggatt ggcgagccac tggtgctgaa gtgtaagggg    120
gcccccaaga accacccca gcggctggaa tggaaactga acacaggccg acagaagct     180
tggaaggtcc tgtctcccca gggaggaggc cctgggaca gtgtggctcg tgtccttccc    240
aacggctccc tcttccttcc ggctgtcggg atccaggatg agggggatttt ccggtgccag    300
gcaatgaaca ggaatggagg atccggtgga ggctccggta ccttagtcac cgtctcctca    360
gagtccaaat atggtccccc atgcccacca tgcccggcgc ctgaggccgc cgggggacca    420
tcagtcttcc tgttcccccc aaaacccaag gacactctca tgatctcccg gacccctgag    480
gtcacgtgcg tggtggtgga cgtgagccag gaagacccc aggtccagtt caactggtac    540
gtggatggcg tggaggtgca taatgccaag acaaagccgc gggaggagca gttcaacagc    600
acgtaccgtg tggtcagcgt cctcaccgtc ctgcaccagg actggctgaa cggcaaggag    660
tacaagtgca aggtctccaa caaaggcctc ccgtcctcca tcgagaaaac catctccaaa    720
gccaaagggc agcctcgaga gccacaggtg tacaccctgc ccccatccca ggaggagatg    780
accaagaacc aggtcagcct gacctgcctg gtcaaaggct tctacccag cgacatcgcc    840
gtggagtggg agagcaatgg gcagccggag aacaactaca agaccacgcc tcccgtgctg    900
gactccgacg gctccttctt cctctacagc aggctaaccg tggacaagag caggtggcag    960
gagggggaatg tcttctcatg ctccgtgatg catgaggctc tgcacaacca ctacacacag   1020
aaaagcttgt ccctgtctct gggtaaatga                                    1050
```

<210> SEQ ID NO 15
<211> LENGTH: 4
<212> TYPE: PRT
<213> ORGANISM: Homo sapiens

<400> SEQUENCE: 15

```
Cys Pro Ser Cys
1
```

<210> SEQ ID NO 16
<211> LENGTH: 8

```
<212> TYPE: PRT
<213> ORGANISM: Homo sapiens

<400> SEQUENCE: 16

Gly Thr Leu Val Thr Val Ser Ser
1               5

<210> SEQ ID NO 17
<211> LENGTH: 15
<212> TYPE: PRT
<213> ORGANISM: Homo sapiens

<400> SEQUENCE: 17

Glu Pro Lys Ser Cys Asp Lys Thr His Thr Cys Pro Pro Cys Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Artificial Hg Variant

<400> SEQUENCE: 18

Glu Pro Lys Ser Ala Asp Lys Thr His Thr Cys Pro Pro Cys Pro
1               5                   10                  15

<210> SEQ ID NO 19
<211> LENGTH: 9
<212> TYPE: PRT
<213> ORGANISM: Homo sapiens

<400> SEQUENCE: 19

Glu Ser Lys Tyr Gly Pro Ser Cys Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Artificial Hg Variant

<400> SEQUENCE: 20

Glu Ser Lys Tyr Gly Pro Pro Cys Pro
1               5

<210> SEQ ID NO 21
<211> LENGTH: 5
<212> TYPE: PRT
<213> ORGANISM: Homo sapiens

<400> SEQUENCE: 21

Cys Pro Pro Cys Pro
1               5

<210> SEQ ID NO 22
<211> LENGTH: 110
<212> TYPE: PRT
<213> ORGANISM: Homo sapiens

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30
```

```
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 23
<211> LENGTH: 110
<212> TYPE: PRT
<213> ORGANISM: Artificial Sequence
<220> FEATURE:
<223> OTHER INFORMATION: Ch2 Variant

<400> SEQUENCE: 23

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 24
<211> LENGTH: 107
<212> TYPE: PRT
<213> ORGANISM: Homo sapiens

<400> SEQUENCE: 24

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 25
<211> LENGTH: 110
<212> TYPE: PRT
```

-continued

<213> ORGANISM: Homo sapiens

<400> SEQUENCE: 25

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 26
<211> LENGTH: 110
<212> TYPE: PRT
<213> ORGANISM: Artificial Sequence
<220> FEATURE:
<223> OTHER INFORMATION: Artificial Ch2 variant

<400> SEQUENCE: 26

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 27
<211> LENGTH: 107
<212> TYPE: PRT
<213> ORGANISM: Homo sapiens

<400> SEQUENCE: 27

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr

```
                    85                  90                  95
Thr Gln Lys Ser Leu Ser Leu Ser Leu Gly Lys
                100                 105

<210> SEQ ID NO 28
<211> LENGTH: 217
<212> TYPE: PRT
<213> ORGANISM: Artificial Sequence
<220> FEATURE:
<223> OTHER INFORMATION: Artificial CH2 - CH3 Variant

<400> SEQUENCE: 28

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 29
<211> LENGTH: 217
<212> TYPE: PRT
<213> ORGANISM: Artificial Sequence
<220> FEATURE:
<223> OTHER INFORMATION: Artificial CH2 - CH3 Variant

<400> SEQUENCE: 29

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
```

```
            65                  70                  75                  80
Gln Asp Trp Leu Asn Gly Lys Glu Tyr Lys Cys Lys Val Ser Asn Lys
                    85                  90                  95
Gly Leu Pro Ser Ser Ile Glu Lys Thr Ile Ser Lys Ala Lys Gly Gln
                    100                 105                 110
Pro Arg Glu Pro Gln Val Tyr Thr Leu Pro Pro Ser Gln Glu Glu Met
                    115                 120                 125
Thr Lys Asn Gln Val Ser Leu Thr Cys Leu Val Lys Gly Phe Tyr Pro
            130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                    165                 170                 175
Tyr Ser Arg Leu Thr Val Asp Lys Ser Arg Trp Gln Glu Gly Asn Val
                    180                 185                 190
Phe Ser Cys Ser Val Met His Glu Ala Leu His Asn His Tyr Thr Gln
                    195                 200                 205
Lys Ser Leu Ser Leu Ser Leu Gly Lys
            210                 215

<210> SEQ ID NO 30
<211> LENGTH: 229
<212> TYPE: PRT
<213> ORGANISM: Homo sapiens

<400> SEQUENCE: 30

Glu Ser Lys Tyr Gly Pro Ser Cys Pro Ser Cys Pro Ala Pro Glu Phe
1               5                   10                  15
Leu Gly Gly Pro Ser Val Phe Leu Phe Pro Pro Lys Pro Lys Asp Thr
                    20                  25                  30
Leu Met Ile Ser Arg Thr Pro Glu Val Thr Cys Val Val Val Asp Val
                    35                  40                  45
Ser Gln Glu Asp Pro Glu Val Gln Phe Asn Trp Tyr Val Asp Gly Val
            50                  55                  60
Glu Val His Asn Ala Lys Thr Lys Pro Arg Glu Gln Phe Asn Ser
65                  70                  75                  80
Thr Tyr Arg Val Val Ser Val Leu Thr Val Leu His Gln Asp Trp Leu
                    85                  90                  95
Asn Gly Lys Glu Tyr Lys Cys Lys Val Ser Asn Lys Gly Leu Pro Ser
                    100                 105                 110
Ser Ile Glu Lys Thr Ile Ser Lys Ala Lys Gly Gln Pro Arg Glu Pro
                    115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                    165                 170                 175
Pro Pro Val Leu Asp Ser Asp Gly Ser Phe Phe Leu Tyr Ser Arg Leu
                    180                 185                 190
Thr Val Asp Lys Ser Arg Trp Gln Glu Gly Asn Val Phe Ser Cys Ser
                    195                 200                 205
Val Met His Glu Ala Leu His Asn His Tyr Thr Gln Lys Ser Leu Ser
            210                 215                 220
Leu Ser Leu Gly Lys
```

<210> SEQ ID NO 31
<211> LENGTH: 229
<212> TYPE: PRT
<213> ORGANISM: Artificial Sequence
<220> FEATURE:
<223> OTHER INFORMATION: Artificial Hg-CH2-CH3 Variant

<400> SEQUENCE: 31

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225
```

<210> SEQ ID NO 32
<211> LENGTH: 4
<212> TYPE: PRT
<213> ORGANISM: Artificial Sequence
<220> FEATURE:
<223> OTHER INFORMATION: Artificial Linker

<400> SEQUENCE: 32

```
Gly Gly Gly Ser
1
```

<210> SEQ ID NO 33
<211> LENGTH: 6
<212> TYPE: PRT
<213> ORGANISM: Artificial Sequence
<220> FEATURE:
<223> OTHER INFORMATION: Artificial Linker

<400> SEQUENCE: 33

Gly Ser Gly Gly Gly Ser
1               5

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
gtccctggaa ggaagcagg                                        19

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
tttggtaccc ctcaaggccc tccag                                 25

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
tttccatggc agccggaaca gcag                                  24

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
tttggtacct ccattcctgt tcattgcctg g                          31

<210> SEQ ID NO 38
<211> LENGTH: 28
<212> TYPE: DNA
<213> ORGANISM: Artificial Sequence
<220> FEATURE:
<223> OTHER INFORMATION: primer

<400> SEQUENCE: 38
tttggtaccg tggctggaat gggtggcc                              28

<210> SEQ ID NO 39
<211> LENGTH: 36
<212> TYPE: DNA
<213> ORGANISM: Artificial Sequence
<220> FEATURE:
<223> OTHER INFORMATION: primer

<400> SEQUENCE: 39
tttgctagcg ccaccatggc agccggaaca gcagtt                     36

<210> SEQ ID NO 40
<211> LENGTH: 33
<212> TYPE: DNA
<213> ORGANISM: Artificial Sequence

```
<220> FEATURE:
<223> OTHER INFORMATION: primer

<400> SEQUENCE: 40
tttggatccg ggaaggcctg ggctgaagct aca                                33

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
tttggatccg tggctggaat gggtggccac aca                                33

<210> SEQ ID NO 42
<211> LENGTH: 75
<212> TYPE: DNA
<213> ORGANISM: Artificial Sequence
<220> FEATURE:
<223> OTHER INFORMATION: primer

<400> SEQUENCE: 42
tttggatcct ccattcctgt tcattgcctg gcaccggaaa atcccctcat cctgaatccc    60
gacagccgga aggaa                                                    75
```